(12) United States Patent
Wright et al.

(10) Patent No.: US 6,417,169 B1
(45) Date of Patent: Jul. 9, 2002

(54) INSULIN-LIKE GROWTH FACTOR II ANTISENSE OLIGONUCLEOTIDE SEQUENCES AND METHODS OF USING SAME TO INHIBIT CELL GROWTH

(75) Inventors: Jim A. Wright; Aiping H. Young, both of Toronto; Yoon S. Lee, Don Mills, all of (CA)

(73) Assignee: Genesense Technologies Inc., Toronto (CA)

( * ) Notice: Subject to any disclaimer, the term of this patent is extended or adjusted under 35 U.S.C. 154(b) by 0 days.

(21) Appl. No.: 09/295,593

(22) Filed: Apr. 22, 1999

Related U.S. Application Data

(60) Provisional application No. 60/082,791, filed on Apr. 23, 1998.

(51) Int. Cl.[7] .................. C07H 21/04; A61K 48/00; C12Q 1/68; C12N 15/86; C12P 19/34
(52) U.S. Cl. ................. 514/44; 435/6; 435/91.1; 435/325; 435/375; 536/24.5; 536/23.1; 536/24.3; 536/24.31; 536/24.33
(58) Field of Search .................. 435/6, 91.1, 91.3, 435/357, 325, 375; 536/23.1, 23.2, 24.5, 24.3, 24.31, 24.33; 514/44

(56) References Cited

U.S. PATENT DOCUMENTS

| | | | |
|---|---|---|---|
| 5,023,252 A | 6/1991 | Hseih | 514/183 |
| 5,034,506 A | 7/1991 | Summerton et al. | 528/391 |
| 5,225,347 A | 7/1993 | Goldberg et al. | 435/320.1 |
| 5,580,859 A | 12/1996 | Felgner et al. | 514/44 |
| 5,719,262 A | 2/1998 | Buchardt et al. | 530/300 |
| 5,766,855 A | 6/1998 | Buchardt et al. | 435/6 |

FOREIGN PATENT DOCUMENTS

| | | | |
|---|---|---|---|
| WO | 9324655 | * | 12/1993 |
| WO | WO 94/08625 | | 4/1994 |

OTHER PUBLICATIONS

Stellar et al PNAS vol. 92, p 11970–11974.*
Crooke et al "Antisense Research & Applications" p 1–50, 1998.*
Branch TIBS Fe. 23, 1998 p 45–50.*
Agrawal, S. "Antisense oligonucleotides: towards clinical trials" Tibtech, Oct. 1996, vol. 14, pp. 376–387.*
Trojan et al., PNAS, vol. 91, p 6088–6092, Jun. 1994.*
Toretsky and Helman, "Involvement of IGF–II in human cancer," Journal of Endocrinology, 149: 367–372, 1996.
Werner and LeRoith, "The role of the insulin–like growth factor system in human cancer," Advances in Cancer Research, 68: 183–223, 1996.
Rogler, et al., "Altered body composition and increased frequency of diverse malignancies in insulin–like growth factor–II transgenic mice," The Journal of Biological Chemistry, 269(19): 13779–13784, 1994.
Bates, et al., "Mammary cancer in transgenic mice expressing insulin–like growth factor II (IGF–II)," British Journal of Cancer, 72: 1189–1193, 1995.
Cullen et al., "Insulin–like growth factor–II overexpression in MCF–7 cells induces phenotypic changes asociated with malignant progression," Molecular Endocrinology, 6(1): 91–100, 1992.

(List continued on next page.)

Primary Examiner—Andrew Wang
Assistant Examiner—Karen A Lacourciere
(74) Attorney, Agent, or Firm—Gray, Cary, Ware & Freidenrich, LLP; Lisa A. Haile

(57) ABSTRACT

This invention relates to oligonucleotides complementary to the IGF-II genes which modulate tumor cell growth in mammals. This invention is also related to methods of using such compounds in inhibiting the growth of tumor cells in mammals. This invention also relates to pharmaceutical compositions comprising a pharmaceutically acceptable excipient and an effective amount of a compound of this invention.

20 Claims, 16 Drawing Sheets

OTHER PUBLICATIONS

Werner, et al., D. "Molecular and cellular aspects of insulin–like growth factor action," Vitamins and Hormones, 48: 1–58, 1994.

Curcio, et al., "Oligonucleotides as modulators of cancer gene expression," Pharmacol. Ther. 74(3): 317–332, 1997.

Narayanan and Akhtar, "Antisense therapy," Current Opinion in Oncology, 8: 509–515, 1996.

Ho and Parkinson, "Antisense oligonucleotides as therapeutics for malignant diseases," Seminars in Oncology, 24(2): 187–202, 1997.

Crooke and Bennett, "Progress in antisense oligonucleotide therapeutics," Annu Rev Pharmacol Toxicol., 36: 107–129, 1996.

Christofori, et al. "A second signal supplied by insulin–like growth factor II in oncogene–induced tumorigenesis," Nature, 369: 414–417, 1994.

El–Badry, et al., "Insulin–like growth factor II acts as an autocrine growth and motility factor in human rhabdomyosarcoma tumors," Cell Growth & Differentiation, 1: 325–331, 1990.

Kim, et al., "Insulin–like growth factor II induced by hypoxia may contribute to angiogenesis of human hepatocellular carcinoma," Cancer Research, 58: 348–351, 1998.

Volpert et al., "The insulin–like growth factor II/mannose 6–phosphate receptor is required for proliferin–induced angiogenesis," Endocrinology. 137(9), 3871–3876, 1996.

Lin, et al., "Antisense oligodeoxynucleotides of IGF–II selectively inhibit growth of human hepatoma cells overproducing IGF–II," J Biochem (Tokyo). 122: 717–722, 1997.

Steller, et al., "Overexpression of the insulin–like growth factor–1 receptor and autocrine stimulation in human cervical cancer cells," Cancer Res. 56(8): 1761–1765, 1996.

Steller, et al., "Insulin–like growth factor II mediates epidermal growth factor–induced mitogenesis in cervical cancer cells," Proc Natl Acad Sci USA, 92(26): 11970–11974, 1995.

Cole, et al., "Overexpression of a transporter gene in a multidrug–resistant human lung cancer cell line," Science 258:1650–1654, 1992.

Nielsen et al., "Sequence–selective recognition of DNA by strand displacement with a thymine–substituted polyamide," Science 254:1497–1500, 1991.

Good and Nielsen, "Inhibition of translation and bacterial growth by peptide nucleic acid targeted to ribosomal RNA," Proc Natl Acad Sci USA, 95: 2073–2076, 1998.

Sullivan, "Development of ribozymes for gene therapy," The Journal of Investigative Dermatology, 103(5): 85S–89S, 1994.

Kimura et al., "Inhiition of IGF–II–stimulated growth of prostate cancer cells by IGF–I receptor specific monoclonal antibody and antisense oligonucleotide of IGF–II messenger RNA," Journal of Urology, 151 (5 Suppl): 367A, Abstract 560, 1994.

Trojan et al., "Gene therapy of murine teratocarcinoma: separate functions for insulin–like growth factors I and II in immunogenicity and diiffernetiation," Proc Natl Acad Sci USA, 91: 6088–6092, 1994.

Ham et al., "Inhibition of hepatocellular carcinoma cell growth by the extract of symphytum offincinale L. and the possible mechanisms for this inhibition," J. Food Sci. Nutr. 2(3): 236–240, 1997.

Baccarini et al., "Detection of anti–sense transcripts of the insulin–like growth factor–2 gene Wilms' tumor," American Journal of Pathology, 143(6): 1535–1542, 1993.

Brunner et al., "Effect of endocrine therapy on growth of T61 human breast cancer xenografts is directly correlated to a specific down–regulation of insulin–like growth factor II (IGF–II)," Eur. J. Cancer, 29A(4): 562–569, 1993.

Lafarge–Frayssinet et al., "Antisense insulin–like growth factor I transferred into a rat hepatoma cell line inhibits tumorigenesis by modulating major histocompatability complex I cell surface expression," Cancer Gene Therapy, 4(5): 276–285, 1997.

* cited by examiner

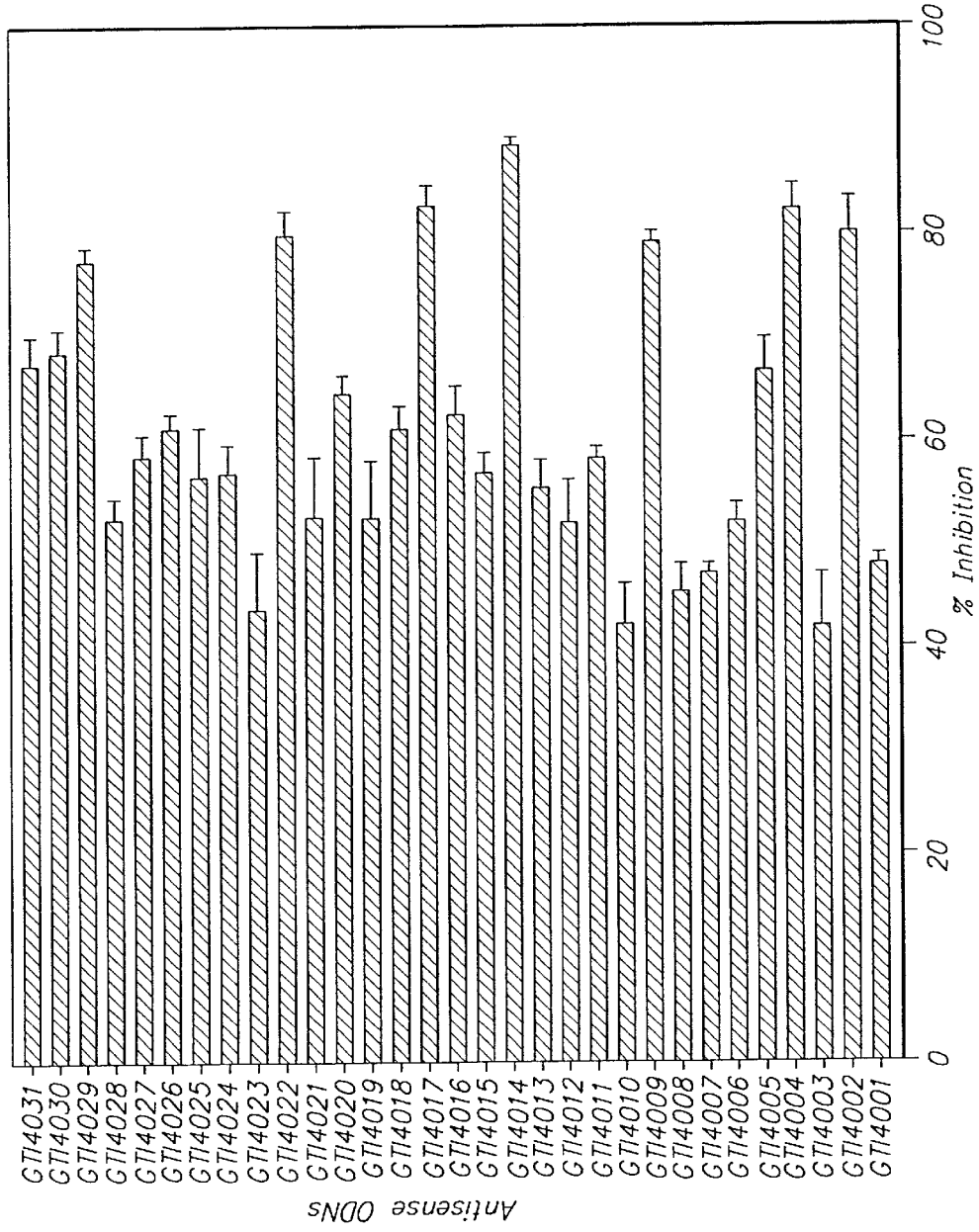

Reduction in IGF-II Protein Expression
in Human Neuroblastoma Cells
by Different Antisense ODNs Exon 4
CCCAAAATTTGGGCATTGTTCCCGCTCGCCGGCCACCCACTGCAGCTTCCCCAACC
CCGCGCACAGCGGGCACTGGTTTCGGGCCTCTCTGTCTCCTACGAAGTCCCCAGAGCAAC
TCGGATTTGGGAAATTTCTCTCTAGCGTTGCCCAAACACACTTGGGTCGGCCGCGCGCCC
TCAGGACGTGGACAGGGAGGGCTTCCCCGTGTCCAGGAAAGCGACCGGGCATTGCCCCCA
GTCTCCCCCAAATTTGGGCATTGTCCCCGGGTCTTCCAACGGACTGGGCGTTGCTCCCGG
ACACTGAGGACTGGCCCCGGGGTCTCGCTCACCTTCAGCAGCGTCCACCGCCTGCCACAG
AGCGTTCGATCGCTCGCTGCCTGAGCTCCTGGTGCGCCCGCGGACGCAGCCTCCAGCTTCGCG

FIG. 11A

Exon 5
GTTCGCCTGCTCTCCGGCGGAGCTGCGTGAGGCCCGGCCGGCCCCGGCCCCCCCCTTCCGGCC
GCCCCCGCCTCCTGGCCCACGCCTGCCCGCGCTCTGCCCACCAGCGCCTCCATCGGGCAAGGC
GGCCCCGCGTCGACGCCGCCCGCTGCCTCGCTGCTGACTCCCGTCCCGGGCGCCGTCCGCGGG
GTCGCGCTCCGCCGGGCCTGCGGATTCCCCGCCGCCTCCTCTTCATCTACCTCAACTCCCCCCA
TCCCCGCTTCGCCCGAGGAGGCGGTTCCCCCCGCAGGCAGTCCGGCTCGCAGGCCGCCGGCGT
TGTCACCCCCCCGCGCTCCCCCTCCAGCCCTCCCCCCGGCGCGCAGCCTCGGGCCGCTCCCCT
TTCCGCGCTGCGTCCCGGAGCGGCCCCGGTGCCGCCACCGCCTGTCCCCCTCCCGAGGCCCGG
GCTCGCGACGGCAGAGGGCTCCGTCGGCCCAAACCGAGCTGGGCGCCCGCGGTCCGGGTGCA
GCCTCCACTCCGCCCCCCAGTCACCGCCTCCCCCGGCCCCTCGACGTGGCGCCCTTCCCTCCGC
TTCTCTGTGCTCCCCGCGCCCCTCTTGGCGTCTGGCCCCGGCCCCCGCTCTTTCTCCCGCAACC
TTCCCTTCGCTCCCTCCCGTCCCCCCAGCTCCTAGCCTCCGACTCCCTCCCCCCCTCACGCCC
GCCCTCTCGCCTTCGCCGAACCAAAGTGGATTAATTACACGCTTTCTGTTTCTCTCCGTGCTGT
TCTCTCCCGCTGTGCGCCTGCCCGCCTCTCGCTGTCCTCTCTCCCCCTCGCCCTCTCTTCGGCCC
CCCCCTTTCACGTTCACTCTGTCTCTCCCACTATCTCTGCCCCCCTCTATCCTTGATACAACAGC
TGACCTCATTTCCCGATACCTTTTCCCCCCCGAAAAGTACAACATCTGGCCCGCCCCAGCCCG
AAGACAGCCCGTCCTCCCTGGACAATCAGACGAATTCTCCCCCCCCCCCCAAAAAAAAGCCAT
CCCCCCGCTCTGCCCCGTCGCACATTCGGCCCCCGCGACTCGGCCAGAGCGGCGCTGGCAGAG
GAGTGTCCGGCAGGAGGGCCAACGCCCGCTGTTCGGTTTGCGACACGCAGCAGGGAGGTGGG
CGGCAGCGTCGCCGGCTTCCAG

FIG. 11B

Exon 6
GCAAACTGGATATTAGCTTCTCCTGTGAAAGAGACTTCCAGCTTCCTCCTCCTCCTCTTCCTCC
TCCTCCTCCTGCCCCAGCGAGCCTTCTGCTGAGCTGTAG

FIG. 11C

Exon 7-9

```
ACACCAATGGGAATCCCAATGGGGAAGTCGATGCTGGTGCTTCTCACCTTCTTGGCCTTCGCC
TCGTGCTGCATTGCTGCTTACCGCCCCAGTGAGACCCTGTGCGGCGGGGAGCTGGTGGACACC
CTCCAGTTCGTCTGTGGGGACCGCGGCTTCTACTTCAGCAGGCCCGCAAGCCGTGTGAGCCGT
CGCAGCCGTGGCATCGTTGAGGAGTGCTGTTTCCGCAGCTGTGACCTGGCCCTCCTGGAGACG
TACTGTGCTACCCCCGCCAAGTCCGAGAGGGACGTGTCGACCCCTCCGACCGTGCTTCCGGAC
AACTTCCCCAGATACCCCGTGGGCAAGTTCTTCCAATATGACACCTGGAAGCAGTCCACCCAG
CGCCTGCGCAGGGGCCTGCCTGCCCTCCTGCGTGCCCGCCGGGGTCACGTGCTCGCCAAGGAG
CTCGAGGCGTTCAGGGAGGCCAAACGTCACCGTCCCCTGATTGCTCTACCCACCCAAGACCCC
GCCCACGGGGCGCCCCCCCAGAGATGGCCAGCAATCGGAAGTGAGCAAAACTGCCGCAAGT
CTGCAGCCCGGCGCCACCATCCTGCAGCCTCCTCCTGACCACGGACGTTTCCATCAGGTTCCA
TCCCGAAAATCTCTCGGTTCCACGTCCCCCTGGGGCTTCTCCTGACCCAGTCCCCGTGCCCCGC
CTCCCCGAAACAGGCTACTCTCCTCGGCCCCCTCCATCGGGCTGAGGAAGCACAGCAGCATCT
TCAAACATGTACAAAATCGATTGGCTTTAAACACCCTTCACATACCCTCCCCCCAAATTATCCC
CAATTATCCCCACACATAAAAAATCAAAACATTAAACTAACCCCCTTCCCCCCCCCCCACAAC
AACCCTCTTAAAACTAATTGGCTTTTTAGAAACACCCCACAAAAGCTCAGAAATTGGCTTTAA
AAAAAACAACCACCAAAAAAAATCAATTGGCTAAAAAAAAAAAGTATTAAAAACGAATTGG
CTGAGAAACAATTGGCAAAATAAAGGAATTTGGCACTCCCCACCCCCTCTTTCTCTTCTCCCT
TGGACTTTGAGTCAAATTGGCCTGGACTTGAGTCCCTGAACCAGCAAAGAGAAAAGAAGGGC
CCCAGAAATCACAGGTGGGCACGTCGCTCGTACCGCCATCTCCCTTCTCACGGGAATTTTCAG
GGTAAACTGGCCATCCGAAAATAGCAACAACCCAGACTGGCTCCTCACTCCCTTTTCCATCAC
TAAAAATCACAGAGCAGTCAGAGGGACCCAGTAAGACCAAAGGAGGGGAGGACAGAGCATG
AAAACCAAAATCCATGCAAATGAAATGTAATTGGCACGACCCTCACCCCCAAATCTTACATCT
CAATTCCCATCCTAAAAAGCACTCATACTTTATGCATCCCCGCAGCTACACACACACAACACA
CAGCACACGCATGAACACAGCACACACACGAGCACAGCACACACACGAGCATACAGCACAC
ACACAAACGCACAGCACACACAGCACACAGATGAGCACACAGCACACACACAAACGCACAG
CACACACACGCACACACATGCACACACAGCACACAAACGCACGGCACACACACGCACACACA
GTGCACACACAGCACACACGCAAACGCACACGCACACACAAACGCACAGCACACACGCACAC
ACAGCACACACACGAGCACACAGCACACAAACGCACAGCACACGCACACACATGCACACAC
AGCACACTAGCACACAGCACACACACAAAGACACAGCACACACATGCACACACAGCACACAC
ACGCGAACACAGCACACACGAACACAGCACACACAGCACACACAAACACAGCACACACA
TGCACACAGCACATGCACACACAGCACACACATGAACACAGCACACAGCACACACATGCACA
CAGCACACACGCATGCACAGCACACATGAACACAGCACACACAAACACACAGCACACACATG
CACACACAGCACACACACTCATGCGCAGCACATACATGAACACAGCTCACAGCACACAAACA
CGCAGCACACACGTTGCACACGCAAGCACCCACCTGCACACACACATGCGCACACACGCA
CACCCCCACAAAATTAGATGAAAACAATAAGCATATCTAAGCAACTACGATATCTGTATGGAT
CAGGCCAAAGTCCCGCTAAGATTCTCCAATGTTTTCATGGTCTGAGCCCCCTCCTGTTCCCAT
CTCCACTGCCCCTCGGCCCTGTCTGTGCCCTGCCTCTCAGAGGAGGGGGCTCAGATGGTGCGG
CCTGAGTGTGCGGCCGGCGGCATTTGGGATACACCCGTAGGTGGGCGGGGTGTGTCCCAGGC
CTAATTCCATCTTTCCACCATGACAGAGATGCCCTTGTGAGGCTGGCCTCCTTGGCGCCTGTCC
CCACGGCCCCCGCAGCGTGAGCCACGATGCTCCCCATACCCCACCCATTCCCGATACACCTTA
CTTACTGTGTGTTGGCCCAGCCAGAGTGAGGAAGGAGTTTGGCCACATTGGAGATGGCCGGTA
GCTGAGCAGACATGCCCCCACGAGTAGCCTGACTCCCTGGTGTGCTCCTGGAAGGAAGATCTT
GGGGACCCCCCCACCGGAGCACACCTAGGGATCATCTTTGCCCGTCTCCTGGGGACCCCCCAA
GAAATGTGGAGTCCTCGGGGCCGTGCACTGATGCGGGGAGTGTGGGAAGTCTGGCGGTTGG
AGGGGTGGGTGGGGGGCAGTGGGGGCTGGGCGGGGGGAGTTCTGGGGTAGGAAGTGGTCCC
GGGAGATTTTGGATGGAAAAGTCAGGAGGATTGACAGCAGACTTGCAGAATTACATAGAGAA
ATTAGGAACCCCCAAATTTCATGTCAATTGATCTATTCCCCCTCTTTGTTTCTTGGGGCATTTTT
CCTTTTTTTTTTTTTTTTGTTTTTTTTTTACCCCTCCTTAGCTTTATGCGCTCAGAAACCAAATTA
```

FIG. 11D

```
AACCCCCCCCCCATGTAACAGGGGGGCAGTGACAAAAGCAAGAACGCACGAAGCCAGCCTGG
AGACCACCACGTCCTGCCCCCCGCCATTTATCGCCCTGATTGGATTTTGTTTTTCATCTGTCCCT
GTTGCTTGGGTTGAGTTGAGGGTGGAGCCTCCTGGGGGGCATGGCCATGAGCCCCCTTGGAGA
AGTCAGAGGGGAGTGGAGAAGGCATGTCCGGCCTGGCTTCTGGGGACAGTGGCTGGTCCCCA
GAAGTCCTGAGGGCGGAGGGGGGGTTGGGCAGGGTCTCCTCAGGTGTCAGGAGGGTGCTCG
GAGGCCACAGGAGGGGGCTCCTGGCTGGCCTGAGGCTGGCCGGAGGGGAAGGGGCTAGCAG
GTGTGTAAACAGAGGGTTCCATCAGCTGGGGCAGGGTGGCCGCCTTCCGCACACTTGAGGAA
CCCTCCCCTCTCCCTCGGTGACATCTTGCCCGCCCCTCAGCACCCTGCCTTGTCTCCAGGAGGT
CCGAAGCTCTGTGGGACCTCTTGGGGGCAAGGTGGGGTGAGGCCGGGGAGTAGGGAGGTCAG
GCGGGTCTGAGCCCACAGAGCAGGAGAGCTGCCAGGTCTGCCCATCGACCAGGTTGCTTGGG
CCCCGGAGCCCACGGGTCTGGTGATGCCATAGCAGCCACCACCGCGGCGCCTAGGGCTGCGG
CAGGGACTCGGCCTCTGGGAGGTTTACCTCGCCCCCACTTGTGCCCCCAGCTCAGCCCCCCTG
CACGCAGCCCGACTAGCAGTCTAGAGGCCTGAGGCTTCTGGGTCCTGGTGACGGGGCTGGCAT
GACCCCGGGGGTCGTCCATGCCAGTCCGCCTCAGTCGCAGAGGGTCCCTCGGCAAGCGCCCTG
TGAGTGGGCCATTCGGAACATTGGACAGAAGCCCAAAGAGCCAAATTGTCACAATTGTGGAA
CCCACATTGGCCTGAGATCCAAAACGCTTCGAGGCACCCCAAATTACCTGCCCATTCGTCAGG
ACACCCACCCACCCAGTGTTATATTCTGCCTCGCCGGAGTGGGTGTTCCCGGGCTGCCTGTCTG
ACCTCCGTGCCTAGTCGTGGCTCTCCATCTTGTCTCCTCCCCGTGTCCCCAATGTCTTCAGTGG
GGGGCCCCCTCTTGGGTCCCCTCCTCTGCCATCACCTGAAGACCCCCACGCCAAACACTGAAT
GTCACCTGTGCCTGCCGCCTCGGTCCACCTTGCGGCCCGTGTTTGACTCAACTCAGCTCCTTTA
ACGCTAATATTTCCGGCAAAATCCCATGCTTGGGTTTTGTCTTTAACCTTGTAACGCTTGCAAT
CCCAATAAAGCATTAAAAGTCA
```

FIG. 11D CONTINUED

SEQUENCE LISTING

<160> NUMBER OF SEQ ID NOS: 37

<210> SEQ ID NO 1
<211> LENGTH: 20
<212> TYPE: DNA
<213> ORGANISM: Human

<400> SEQUENCE: 1
ggctcgctgg ggcaggagga                                            20

<210> SEQ ID NO 2
<211> LENGTH: 20
<212> TYPE: DNA
<213> ORGANISM: Human

<400> SEQUENCE: 2
gctggtgggc agagcgcggg                                            20

<210> SEQ ID NO 3

```
<211> LENGTH: 20
<212> TYPE: DNA
<213> ORGANISM: Human

<400> SEQUENCE: 3
ttggtgtcta cagctcagca                                              20

<210> SEQ ID NO 4
<211> LENGTH: 20
<212> TYPE: DNA
<213> ORGANISM: Human

<400> SEQUENCE: 4
cagcgaggca gcgggcggcg                                              20

<210> SEQ ID NO 5
<211> LENGTH: 20
<212> TYPE: DNA
<213> ORGANISM: Human

<400> SEQUENCE: 5
tcgggcgaag cggggatggg                                              20

<210> SEQ ID NO 6
<211> LENGTH: 20
<212> TYPE: DNA
<213> ORGANISM: Human

<400> SEQUENCE: 6
cgggcctcgg gagggggaca                                              20

<210> SEQ ID NO 7
<211> LENGTH: 20
<212> TYPE: DNA
<213> ORGANISM: Human

<400> SEQUENCE: 7
gaccgcgggc gcccagctcg                                              20

<210> SEQ ID NO 8
<211> LENGTH: 20
<212> TYPE: DNA
<213> ORGANISM: Human

<400> SEQUENCE: 8
acgtcgaggg gccgggggag                                              20

<210> SEQ ID NO 9
<211> LENGTH: 20
<212> TYPE: DNA
<213> ORGANISM: Human

<400> SEQUENCE: 9
cgggagaaag agcgggggcc                                              20

<210> SEQ ID NO 10
<211> LENGTH: 20
<212> TYPE: DNA
<213> ORGANISM: Human

<400> SEQUENCE: 10
cgagagggcg ggcgtgaggg                                              20
```

-continued

```
<210> SEQ ID NO 11
<211> LENGTH: 20
<212> TYPE: DNA
<213> ORGANISM: Human

<400> SEQUENCE: 11
cagcgagagg cgggcaggcg                                                    20

<210> SEQ ID NO 12
<211> LENGTH: 20
<212> TYPE: DNA
<213> ORGANISM: Human

<400> SEQUENCE: 12
cgggctgtct tcgggctggg                                                    20

<210> SEQ ID NO 13
<211> LENGTH: 20
<212> TYPE: DNA
<213> ORGANISM: Human

<400> SEQUENCE: 13
gcgacggggc agagcggggg                                                    20

<210> SEQ ID NO 14
<211> LENGTH: 20
<212> TYPE: DNA
<213> ORGANISM: Human

<400> SEQUENCE: 14
cgctgccgcc cacctccctg                                                    20

<210> SEQ ID NO 15
<211> LENGTH: 20
<212> TYPE: DNA
<213> ORGANISM: Human

<400> SEQUENCE: 15
ttggtgtctg gaagccggcg                                                    20

<210> SEQ ID NO 16
<211> LENGTH: 20
<212> TYPE: DNA
<213> ORGANISM: Human

<400> SEQUENCE: 16
ttccccattg ggattcccat                                                    20

<210> SEQ ID NO 17
<211> LENGTH: 20
<212> TYPE: DNA
<213> ORGANISM: Human

<400> SEQUENCE: 17
gtccaccagc tccccgccgc                                                    20

<210> SEQ ID NO 18
<211> LENGTH: 20
<212> TYPE: DNA
<213> ORGANISM: Human

<400> SEQUENCE: 18
cgatgccacg gctgcgacgg                                                    20
```

```
<210> SEQ ID NO 19
<211> LENGTH: 20
<212> TYPE: DNA
<213> ORGANISM: Human

<400> SEQUENCE: 19
acgcaggagg gcaggcaggc                                              20

<210> SEQ ID NO 20
<211> LENGTH: 20
<212> TYPE: DNA
<213> ORGANISM: Human

<400> SEQUENCE: 20
gcgagcacgt gaccccggcg                                              20

<210> SEQ ID NO 21
<211> LENGTH: 20
<212> TYPE: DNA
<213> ORGANISM: Human

<400> SEQUENCE: 21
cgtgggcggg gtcttgggtg                                              20

<210> SEQ ID NO 22
<211> LENGTH: 20
<212> TYPE: DNA
<213> ORGANISM: Human

<400> SEQUENCE: 22
tgtttcgggg aggcgggggca                                             20

<210> SEQ ID NO 23
<211> LENGTH: 20
<212> TYPE: DNA
<213> ORGANISM: Human

<400> SEQUENCE: 23
gcggtacgag cgacgtgccc                                              20

<210> SEQ ID NO 24
<211> LENGTH: 20
<212> TYPE: DNA
<213> ORGANISM: Human

<400> SEQUENCE: 24
caaatgccgc cggccgcaca                                              20

<210> SEQ ID NO 25
<211> LENGTH: 20
<212> TYPE: DNA
<213> ORGANISM: Human

<400> SEQUENCE: 25
cgcatcagtg cacggccccc                                              20

<210> SEQ ID NO 26
<211> LENGTH: 20
<212> TYPE: DNA
<213> ORGANISM: Human

<400> SEQUENCE: 26
gtgcggaagg cggccaccct                                              20
```

<210> SEQ ID NO 27
<211> LENGTH: 20
<212> TYPE: DNA
<213> ORGANISM: Human

<400> SEQUENCE: 27
cagggtgctg aggggcgggc            20

<210> SEQ ID NO 28
<211> LENGTH: 20
<212> TYPE: DNA
<213> ORGANISM: Human

<400> SEQUENCE: 28
gctccggggc ccaagcaacc            20

<210> SEQ ID NO 29
<211> LENGTH: 20
<212> TYPE: DNA
<213> ORGANISM: Human

<400> SEQUENCE: 29
ccctaggcgc cgcggtggtg            20

<210> SEQ ID NO 30
<211> LENGTH: 20
<212> TYPE: DNA
<213> ORGANISM: Human

<400> SEQUENCE: 30
tggcatggac gaccccgggg            20

<210> SEQ ID NO 31
<211> LENGTH: 20
<212> TYPE: DNA
<213> ORGANISM: Human

<400> SEQUENCE: 31
gggccgcaag gtggaccgag            20

<210> SEQ ID NO 32
<211> LENGTH: 20
<212> TYPE: DNA
<213> ORGANISM: Human

<400> SEQUENCE: 32
taccgcccca gtgagaccct            20

<210> SEQ ID NO 33
<211> LENGTH: 20
<212> TYPE: DNA
<213> ORGANISM: Human

<400> SEQUENCE: 33
tgacgtttgg cctccctgaa            20

<210> SEQ ID NO 34
<211> LENGTH: 419
<212> TYPE: DNA
<213> ORGANISM: Human

<400> SEQUENCE: 34

-continued

| | |
|---|---|
| cccaaaattt gggcattgtt cccgctcgcc ggccacccac tgcagcttcc ccaacccgc | 60 |
| gcacagcggg cactggtttc gggcctctct gtctcctacg aagtcccag agcaactcgg | 120 |
| atttgggaaa tttctctcta gcgttgccca aacacacttg ggtcggccgc gcgccctcag | 180 |
| gacgtggaca gggagggctt ccccgtgtcc aggaaagcga ccgggcattg cccccagtct | 240 |
| cccccaaatt tgggcattgt cccgggtct tccaacggac tgggcgttgc tcccggacac | 300 |
| tgaggactgg ccccggggtc tcgctcacct tcagcagcgt ccaccgcctg ccacagagcg | 360 |
| ttcgatcgct cgctgcctga gctcctggtg cgcccgcgga cgcagcctcc agcttcgcg | 419 |

<210> SEQ ID NO 35
<211> LENGTH: 1164
<212> TYPE: DNA
<213> ORGANISM: Human

<400> SEQUENCE: 35

| | |
|---|---|
| gttcgcctgc tctccggcgg agctgcgtga ggcccggccg gccccggccc ccccttccg | 60 |
| gccgccccg cctcctggcc cacgcctgcc cgcgctctgc ccaccagcgc ctccatcggg | 120 |
| caaggcggcc ccgcgtcgac gccgcccgct gcctcgctgc tgactcccgt cccgggcgcc | 180 |
| gtccgcgggg tcgcgctccg ccgggcctgc ggattccccg ccgcctcctc ttcatctacc | 240 |
| tcaactcccc ccatccccgc ttcgcccgag gaggcggttc ccccgcagg cagtccggct | 300 |
| cgcaggccgc cggcgttgtc accccccccg cgctcccct ccagccctcc cccggcgcg | 360 |
| cagcctcggg ccgctccct ttcgcgctg cgtcccggag cggcccggt gccgccaccg | 420 |
| cctgtccccc tcccgaggcc cgggctcgcg acggcagagg gctccgtcgg cccaaaccga | 480 |
| gctgggcgcc cgcggtccgg gtgcagcctc cactccgccc ccagtcacc gcctcccccg | 540 |
| gcccctcgac gtggcgccct tccctccgct tctctgtgct cccgcgcgcc ctcttggcgt | 600 |
| ctggcccgg ccccgctct ttctcccgca accttccctt cgctccctcc cgtcccccc | 660 |
| agctcctagc ctccgactcc ctccccccct cacgcccgcc ctctcgcctt cgccgaacca | 720 |
| aagtggatta attacacgct ttctgtttct ctccgtgctg ttctctcccg ctgtgcgcct | 780 |
| gcccgcctct cgctgtcctc tctccccctc gccctctctt cggccccccc ctttcacgtt | 840 |
| cactctgtct ctcccactat ctctgccccc ctctatcctt gatacaacag ctgacctcat | 900 |
| ttcccgatac cttttccccc ccgaaaagta caacatctgg cccgcccag cccgaagaca | 960 |
| gcccgtcctc cctggacaat cagacgaatt ctcccccccc cccaaaaaa aagccatccc | 1020 |
| cccgctctgc cccgtcgcac attcggcccc cgcgactcgg ccagagcggc gctggcagag | 1080 |
| gagtgtccgg caggagggcc aacgcccgct gttcggtttg cgacacgcag cagggaggtg | 1140 |
| ggcggcagcg tcgccggctt ccag | 1164 |

<210> SEQ ID NO 36
<211> LENGTH: 103
<212> TYPE: DNA
<213> ORGANISM: Human

<400> SEQUENCE: 36

| | |
|---|---|
| gcaaactgga tattagcttc tcctgtgaaa gagacttcca gcttcctcct cctcctcttc | 60 |
| ctcctcctcc tcctgcccca gcgagccttc tgctgagctg tag | 103 |

<210> SEQ ID NO 37
<211> LENGTH: 4350
<212> TYPE: DNA
<213> ORGANISM: Human

<400> SEQUENCE: 37

```
acaccaatgg gaatcccaat ggggaagtcg atgctggtgc ttctcacctt cttggccttc        60
gcctcgtgct gcattgctgc ttaccgcccc agtgagaccc tgtgcggcgg ggagctggtg       120
gacaccctcc agttcgtctg tggggaccgc ggcttctact tcagcaggcc cgcaagccgt       180
gtgagccgtc gcagccgtgg catcgttgag gagtgctgtt tccgcagctg tgacctggcc       240
ctcctggaga cgtactgtgc tacccccgcc aagtccgaga gggacgtgtc gaccccctccg      300
accgtgcttc cggacaactt ccccagatac cccgtgggca agttcttcca atatgacacc       360
tggaagcagt ccacccagcg cctgcgcagg ggcctgcctg ccctcctgcg tgcccgccgg       420
ggtcacgtgc tcgccaagga gctcgaggcg ttcaggcagg ccaaacgtca ccgtcccctg       480
attgctctac ccacccaaga ccccgcccac ggggcgccc cccagagat ggccagcaat         540
cggaagtgag caaaactgcc gcaagtctgc agcccgcgc accatcctg cagcctcctc         600
ctgaccacgg acgtttccat caggttccat cccgaaaatc tctcggttcc acgtcccct       660
ggggcttctc ctgacccagt ccccgtgccc cgcctcccg aaacaggcta ctctcctcgg        720
ccccctccat cgggctgagg aagcacagca gcatcttcaa acatgtacaa aatcgattgg       780
cttaaacac ccttcacata ccctccccccc aaattatccc caattatccc cacacataaa      840
aaatcaaaac attaaactaa ccccctcccc ccccccccac aacaacctc ttaaaactaa       900
ttggcttttt agaaacaccc cacaaaagct cagaaattgg ctttaaaaaa aacaaccacc       960
aaaaaaaatc aattggctaa aaaaaaaaag tattaaaaac gaattggctg agaaacaatt     1020
ggcaaaataa aggaatttgg cactccccac cccctctttt ctcttctccc ttggactttg     1080
agtcaaattg gcctggactt gagtccctga accagcaaag agaaagaag ggccccagaa      1140
atcacaggtg ggcacgtcgc tcgtaccgcc atctcccttc tcacgggaat tttcagggta    1200
aactggccat ccgaaaatag caacaaccca gactggctcc tcactcccttt tccatcact    1260
aaaaatcaca gagcagtcag agggacccag taagaccaaa ggaggggagg acagagcatg    1320
aaaccaaaa tccatgcaaa tgaaatgtaa ttggcacgac cctcaccccc aaatcttaca     1380
tctcaattcc catcctaaaa agcactcata ctttatgcat ccccgcagct acacacacac    1440
aacacacagc acacgcatga acacagcaca cacgcagca cagcacacac acgagcatac     1500
agcacacaca caaacgcaca gcacacacag cacacagatg agcacacagc acacacaa      1560
acgcacagca cacacgca cacacatgca cacacagcac acaaacgcac ggcacacaca      1620
cgcacacaca gtgcacacac agcacacacg caaacgcaca cgcacacaca aacgcacagc    1680
acacgcac acacagcaca cacgagca cacagcacac aaacgcacag cacacgcaca       1740
cacatgcaca cacagcacac tagcacacag cacacacaca aagacacagc acacacatgc   1800
acacacagca cacacgcg aacacagcac acacgaaca gcacacaca gcacacac        1860
aaacacagca cacacatgca cacagcacat gcacacacag cacacacatg aacacagcac    1920
acagcacaca catgcacaca gcacacacgc atgcacagca cacatgaaca cagcacacac    1980
aaacacacag cacacacatg cacacacagc acacacactc atgcgcagca catacatgaa    2040
cacagctcac agcacacaaa cacgcagcac acacgttgca cacgcaagca cccacctgca    2100
cacacacatg cgcacacaca cgcacacccc cacaaaatta gatgaaaaca ataagcatat    2160
ctaagcaact acgatatctg tatggatcag gccaaagtcc cgctaagatt ctccaatgtt    2220
ttcatggtct gagcccccct cctgttccca tctccactgc ccctcggccc tgtctgtgcc    2280
```

-continued

```
ctgcctctca gaggaggggg ctcagatggt gcggcctgag tgtgcggccg gcggcatttg      2340
ggatacaccc gtaggtgggc ggggtgtgtc ccaggcctaa ttccatcttt ccaccatgac      2400
agagatgccc ttgtgaggct ggcctccttg gcgcctgtcc ccacgccccc cgcagcgtga      2460
gccacgatgc tccccatacc ccacccattc ccgatacacc ttacttactg tgtgttggcc      2520
cagccagagt gaggaaggag tttggccaca ttggagatgg ccgtagctg agcagacatg       2580 cccccacgag tagcctgact ccctggtgtg ctcctggaag aagatcttg ggaccccccc       2640 caccggagca cacctaggga tcatctttgc ccgtctcctg ggaccccccc aagaaatgtg      2700
gagtcctcgg gggccgtgca ctgatgcggg gagtgtggga agtctggcgg ttggaggggt     2760
gggtgggggg cagtggggc tgggcggggg gagttctggg gtaggaagtg gtcccgggag      2820
attttggatg gaaaagtcag gaggattgac agcagacttg cagaattaca tagagaaatt      2880
aggaaccccc aaatttcatg tcaattgatc tattccccct cttttgtttct tgggcatttt     2940 ttccttttt tttttttttt gtttttttttt taccccctcct tagctttatg cgctcagaaa    3000
ccaaattaaa cccccccccc atgtaacagg ggggcagtga caaaagcaag aacgcacgaa      3060
gccagcctgg agaccaccac gtcctgcccc ccgccattta tcgccctgat tggatttgt      3120 ttttcatctg tccctgttgc ttgggttgag ttgagggtgg agcctcctgg ggggcatggc     3180
catgagcccc cttggagaag tcagagggga gtggagaagg catgtccggc ctggcttctg     3240
gggacagtgg ctggtcccca gaagtcctga gggcggaggg gggggttggg cagggtctcc     3300
tcaggtgtca ggagggtgct cggaggccac aggagggggc tcctggctgg cctgaggctg     3360
gccggagggg aagggctag cagtgtgta acagagggt tccatcagct ggggcagggt        3420
ggccgccttc cgcacacttg aggaaccctc ccctctccct cggtgacatc ttgcccgccc     3480
ctcagcaccc tgccttgtct ccaggaggtc cgaagctctg tgggacctct tgggggcaag    3540
gtggggtgag gccggggagt agggaggtca ggcgggtctg agcccacaga gcaggagagc     3600
tgccaggtct gccatcgac caggttgctt gggccccgga gcccacgggt ctggtgatgc      3660
catagcagcc accaccgcgg cgcctagggc tcggcaggg actcggcctc tgggaggttt     3720
acctcgcccc cacttgtgcc cccagctcag ccccctgca cgcagcccga ctagcagtct      3780
agaggcctga ggcttctggg tcctggtgac ggggctggca tgaccccggg ggtcgtccat    3840
gccagtccgc ctcagtcgca gagggtccct cggcaagcgc cctgtgagtg ggccattcgg    3900
aacattggac agaagcccaa agagccaaat tgtcacaatt gtggaaccca cattggcctg     3960
agatccaaaa cgcttcgagg cacccccaaat tacctgccca ttcgtcagga cacccaccca    4020
cccagtgtta tattctgcct cgccggagtg ggtgttcccg ggctgcctgt ctgacctccg     4080
tgcctagtcg tggctctcca tcttgtctcc tccccgtgtc cccaatgtct tcagtggggg     4140 gcccctctt gggtcccctc ctctgccatc acctgaagac cccacgcca aacactgaat       4200 gtcacctgtg cctgccgcct cggtccacct tgcggcccgt gtttgactca actcagctcc     4260
tttaacgcta atatttccgg caaatcccca tgcttgggtt ttgtctttaa ccttgtaacg     4320
cttgcaatcc caataaagca ttaaaagtca                                      4350
```

INSULIN-LIKE GROWTH FACTOR II ANTISENSE OLIGONUCLEOTIDE SEQUENCES AND METHODS OF USING SAME TO INHIBIT CELL GROWTH

REFERENCE TO RELATED APPLICATIONS

This application claims priority to U.S. Provisional Application Serial No. 60/082,791 filed Apr. 23, 1998, which application is incorporated herein by reference in its entirety.

BACKGROUND OF THE INVENTION

1. Field of the Invention

This invention relates to oligonucleotides that are complementary to mammalian insulin-like growth factor II (IGF II) genes which oligonucleotides modulate tumor cell growth in mammals. This invention is also related to methods of using such compounds in inhibiting the growth of tumor cells in mammals. This invention also relates to pharmaceutical compositions comprising a pharmaceutically acceptable excipient and an effective amount of a compound of this invention.

2. References

The following publications, patent applications and patents are cited in this application:

1. Toretsky, J. A. and Helman, L. J. Involvement of IGF-II in human cancer, J Endocrinol. 149: 367–72, 1996.
2. Werner, H. and LeRoith, D. The role of the insulin-like growth factor system in human cancer, Adv Cancer Res. 68: 183–223, 1996.
3. Rogler, C. E., Yang, D., Rossetti, L., Donohoe, J., Alt, E., Chang, C. J., Rosenfeld, R., Neely, K., and Hintz, R. Altered body composition and increased frequency of diverse malignancies in insulin-like growth factor-II transgenic mice, J Biol Chem. 269: 13779–84, 1994.
4. Bates, P., Fisher, R., Ward, A., Richardson, L., Hill, D. J., and Graham, C. F. Mammary cancer in transgenic mice expressing insulin-like growth factor II (GF-II) [see comments], Br J Cancer. 72: 1189–93, 1995.
5. Cullen, K. J., Lippman, M. E., Chow, D., Hill, S., Rosen, N., and Zwiebel, J. A. Insulin-like growth factor-II overexpression in MCF-7 cells induces phenotypic changes associated with malignant progression, Mol Endocrinol. 6: 91–100, 1992.
6. Werner, H., Adamo, M., Roberts, C. T., Jr., and LeRoith, D. Molecular and cellular aspects of insulin-like growth factor action, Vitam Horm. 48: 1–58, 1994.
7. Curcio, L. D., Bouffard, D. Y., and Scanlon, K. J. Oligonucleotides as modulators of cancer gene expression, Pharmacol Ther. 74: 317–32, 1997.
8. Narayanan, R. and Akhtar, S. Antisense therapy, Curr Opin Oncol. 8: 509–15, 1996.
9. Ho, P. T. and Parkinson, D. R. Antisense oligonucleotides as therapeutics for malignant diseases, Semin Oncol. 24: 187–202, 1997.
10. Crooke, S. T. and Bennett, C. F. Progress in antisense oligonucleotide therapeutics, Annu Rev Pharmacol Toxicol. 36: 107–29, 1996.
11. Christofori, G., Naik, P., and Hanahan, D. A second signal supplied by insulin-like growth factor II in oncogene-induced tumorigenesis, Nature. 369: 414–8, 1994.
12. El-Badry, O. M., Minniti, C., Kohn, E. C., Houghton, P. J., Daughaday, W. H., and Helman, L. J. Insulin-like growth factor II acts as an autocrine growth and motility factor in human rhabdomyosarcoma tumors, Cell Growth Differ. 1: 325–31, 1990.
13. Kim, K. W., Bae, S. K., Lee, O. H., Bae, M. H., Lee, M. J., and Park, B. C. Insulin-like growth factor II induced by hypoxia may contribute to angiogenesis of human hepatocellular carcinoma, Cancer Res. 58: 348–51, 1998.
14. Volpert, O., Jackson, D., Bouck, N., and Linzer, D. I. The insulin-like growth factor II/mannose 6-phosphate receptor is required for proliferin-induced angiogenesis, Endocrinology. 137: 3871–6, 1996.
15. Lin, S. B., Hsieh, S. H., Hsu, H. L., Lai, M. Y., Kan, L. S., and Au, L. C. Antisense oligodeoxynucleotides of IGF-II selectively inhibit growth of human hepatoma cells overproducing IGF-II, J Biochem (Tokyo). 122: 717–22, 1997.
16. Steller, M. A., Delgado, C. H., Bartels, C. J., Woodworth, C. D., and Zou, Z. Overexpression of the insulin-like growth factor-1 receptor and autocrine stimulation in human cervical cancer cells, Cancer Res. 56: 1761–5, 1996.
17. Steller, M. A., Delgado, C. H., and Zou, Z. Insulin-like growth factor II mediates epidermal growth factor-induced mitogenesis in cervical cancer cells, Proc Natl Acad Sci U S A. 92: 11970–4, 1995.
18. Choy et al., "Molecular mechanisms of drug resistance involving ribonucleotide reductase: hydroxyurea resistance in a series of clonally related mouse cell lines selected in the presence of increasing drug concentrations" Cancer Res. 48:2029–2035 (1988) 19. Fan et al., "Ribonucleotide reductase R2 component is a novel malignancy determinant that cooperates with activated oncogenes to determine transformation and malignant potential" Proc. Natl. Acad. Sci USA 93:14036–40 (1996)
20. Huang and Wright, "Fibroblast growth factor mediated alterations in drug resistance and evidence of gene amplification" Oncogene 9:491–499 (1994)
21. Uhlmann et al. Chem Rev. 90:534–583 (1990)
22. Agrawal et al. Trends Biotechnol. 10:152–158 (1992)
23. Remington's Pharmaceutical Sciences, Mace Publishing Company, Philadelphia Pa. 17$^{th}$ ed. (1985)
24. Sambrook et al., Molecular Cloning: A Laboratory Manual, Cold Spring Harbor Laboratory, New York (1989, 1992)
25. Ausubel et al., Current Protocols in Molecular Biology, John Wiley and Sons, Baltimore Md. (1989)
26. Perbal, A Practical Guide to Molecular Cloning, John Wiley & Sons, New York (1988)
27. Hurta and Wright, "Malignant transformation by H-ras results in aberrant regulation of ribonucleotide reductase gene expression by transforming growth factor-beta" J. Cell Biochem 57:543–556 (1995)
28. Dreeley et al., Science, 258:1650–1654 (1992)
29. Nielsen et al.; Science (1991) 354:1497
30. Good and Nielsen; "Inhibition of translation and bacterial growth by peptide nucleic acid targeted to ribosomal RNA", PNAS USA (1998) 95:2073–2076
31. Buchardt, deceased, et al., U.S. Pat. No. 5,766,855
32. Buchardt, deceased, et al., U.S. Pat. No. 5,719,262
33. U.S. Pat. No. 5,034,506
34. Altschul, et al. "Basic local alignment search tool", J. Mol. Biol. (1990) 215:403–10;

35. Devereux J. et al., "A comprehensive set of sequence analysis programs for the VAX", *Nucleic Acids Res.* (1984) 12:387–395;
36. Chang et al.; Somatic Gene Therapy, CRC Press, Ann Arbor Mich. (1995);
37. Vega et al.; *Gene Targeting*, CRC Press, Ann Arbor Mich. (1995)
38. *Vectors: A Survey of Molecular Cloning Vectors and Their Uses*, Butterworths, Boston Mass. (1988)
39. Sullivan, U.S. Pat. No. 5,225,347
40. U.S. Pat. No. 5,023,252, issued Jun. 11, 1991
41. Felgner et al., U.S. Pat. No. 5,580,859

All of the above publications, patent applications and patents are herein incorporated by reference in their entirety to the same extent as if each individual publication, patent application or patent was specifically and individually indicated to be incorporated by reference in its entirety.

3. State of the Art

Insulin-like growth factor II (IGF-II) is a 67 amino acid polypeptide growth factor that is widely expressed in the developing human embryonic tissues and is related to the growth and differentiation of various tissues. After birth, the expression is progressively extinguished in almost all human tissues. In adult humans, serum levels of approximately 100 ng/ml are mainly produced by the liver. The biological functions of IGF-II are mediated through its binding to either the IGF-II receptor (related to carbohydrate metabolism, motility of malignant cells and/or tumor-induced angiogenesis) or the IGF-I receptor (related to signal transduction pathway and mitogenesis).

IGF-II has been implicated in tumor progression and metastasis by a variety of mechanisms in many tumors (reviewed in (1, 2)). Tumors with extensive involvement of IGF-II include childhood tumors such as rhabdomyosarcoma, Wilms' tumor and neuroblastoma. These tumors demonstrate overexpression of IGF-II, show existence of a paracrine or autocrine loop and result in inhibition of tumor growth or metastasis upon blockage of the loop. IGF-II contributes to tumor growth and metastasis to varying degrees in a variety of tumors including osteosarcoma, breast carcinoma, hepatoblastoma, germ cell tumors, hepatocellular carcinoma, adrenocortical carcinoma, lung tumors, leiomyosarcoma, brain tumors and colon carcinoma. Furthermore, the direct role of IGF-II in oncogenesis has been elucidated by transgenic mice and human cell lines overexpressing it (3–5).

The human IGF-II gene is located on chromosome 11p15 just downstream of insulin gene and spans 30 kb (reviewed in (6) ;see FIG. 1). It consists of 9 exons of which exons 7, 8 and part of 9 encode a precursor protein. Exons 1, 4, 5, and 6 are each preceded by distinct promoters P1, P2, P3 and P4. Promoter P1 is active only in adult liver, while P2–4 are active in most fetal tissues. There are a few adult tissues that express low amount of transcripts from P2, 3 and 4 (fetal transcripts). Four major mRNA species (6 Kb, 4.8–5 Kb and 2.2 Kb for fetal transcripts and 5.3 Kb for adult transcript) have been identified which are generated from distinct promoters and by differential splicing. It appears that overexpression of IGF-II observed in various primary cancers and cell lines results from reactivation (in liver) or overexpression (in other organs) of fetal mRNA species whose expression is mainly derived from P3 and P4. These fetal transcripts contain unique 5' untranslated regions (5'UTR containing exons 4 or 5 or 6) that are absent in the adult transcript derived from P1(5'UTR containing exons 1, 2 and 3).

Antisense oligonucleotides (AS-ODNs) have been widely utilized to inhibit gene expression in a target-specific manner by sequence-specific hybridization to target mRNA. In numerous studies, antisense oligonucleotide-mediated repression of oncogenes has revealed that these compounds are not only extremely useful for delineating biochemical mechanisms governing oncogenesis (7), but also considerably promising as novel therapeutic compounds for the treatment of human cancer (8, 9). In addition, relatively less toxicity has been attributed to oligonucleotide-based therapeutics (10).

A few studies (11, 15–17) have shown that certain antisense oligonucleotides targeted against human or mouse adult IGF-II transcripts were effective in interfering with tumor cell proliferation in vitro. In one study (15), the suppression of IGF-II production by an antisense oligonucleotide targeting the translation start site of human adult transcript has resulted in growth inhibition of human hepatocellular carcinoma cell lines, HuH-7 and HepG2. In another studies (16,17) utilizing human cervical cancer cell line, an antisense oligonucleotide targeting the protein coding region of IGF-II was shown to inhibit epidermal growth factor (EGF)-induced mitogenic effect.

Therefore, it would be desirable to identify antisense oligonucleotides directed against IGF-II which act to inhibit the expression and production of IGF-II with higher specificity and with less toxicity.

SUMMARY OF THE INVENTION

This invention is directed to antisense oligonucleotides which modulate the expression of the IGF-II genes and production of IGF-II in mammals and pharmaceutical compositions comprising such antisense oligonucleotides. This invention is also related to methods of using such antisense oligonucleotides for inhibiting tumor growth and metastasis in mammals.

Accordingly, in one of its composition aspects, this invention is directed to an antisense oligonucleotide, which oligonucleotide from about 3 to about 100 nucleotides comprising nucleotides complementary to the mammalian fetal IGF-II mRNA. The antisense oligonucleotide may be nuclease resistant and may have one or more phosphorothioate internucleotide linkages. The antisense oligonucleotide may further comprise additional nucleotides which are not complementary to the IGF-II mRNA. The oligonucleotides may comprise a sequence selected from group consisting of SEQ ID NOs:1 to 15 from Table 1.

This invention is also directed to an antisense oligonucleotide, which oligonucleotide from about 20 to about 100 nucleotides comprising nucleotides complementary to the mammalian adult IGF-II mRNA selected from the group consisting of SEQ ID NOs:17–31 from Table 2.

In another of its composition aspects, this invention is directed to a vector comprising an antisense oligonucleotide sequence from about 3 to 100 nucleotides comprising a sequence complementary to the 5' untranslated region of mammalian fetal IGF-II mRNA.

In another of its composition aspects, this invention is directed to a vector comprising an antisense oligonucleotide sequence from about 20 to 100 nucleotides comprising a sequence selected from the group consisting of SEQ ID NOs: 17–31 in Table 2.

In still another of its composition aspects, this invention is directed to a pharmaceutical composition comprising a pharmaceutically acceptable excipient and an effective amount of an antisense oligonucleotide from about 3 to about 100 nucleotides comprising nucleotides complementary to the mammalian fetal IGF-II mRNA. The oligonucleotides may comprise a sequence selected from group consisting of SEQ ID NOs:1 to 15 from Table 1.

In still another of its composition aspects, this invention is directed to a pharmaceutical composition comprising a pharmaceutically acceptable excipient and an effective amount of an antisense oligonucleotide from about 20 to about 100 nucleotides comprising a sequence selected from the group consisting of SEQ ID NOs:17–31 from Table 2.

In one of its method aspects, this invention is directed to a method for inhibiting the growth of a mammalian tumor comprising, administering to a mammal suspected of having the tumor an effective amount of an antisense oligonucleotide from about 3 nucleotides to about 100 nucleotides complementary to mammalian fetal IGF-1 mRNA under conditions such that the growth of the tumor is inhibited. The antisense oligonucleotide may be administered with a chemotherapeutic agent. The oligonucleotide may comprise a sequence selected from group consisting of SEQ ID NOs:1 to 15 from Table 1.

This invention is also directed to a method for inhibiting the growth of a mammalian tumor comprising, administering to a mammal suspected of having the tumor an effective amount of an antisense oligonucleotide from about 20 nucleotides to about 100 nucleotides complementary to mammalian adult IGF-II mRNA selected from the group consisting of SEQ ID NOs:17–31 from Table 2 under conditions such that the growth of the tumor is inhibited.

In another of its method aspects, this invention is directed to a method for inhibiting the metastasis of a mammalian tumor comprising, administering to a mammal suspected of having a metastatic tumor an effective amount of an antisense oligonucleotide from about 3 nucleotides to about 100 nucleotides complementary to the mammalian fetal IGF-II mRNA under conditions such that the metastasis of the tumor is inhibited. The antisense oligonucleotide may be administered with a chemotherapeutic agent. The oligonucleotides may comprise a sequence selected from group consisting of SEQ ID NOs:1 to 15 from Table 1.

This invention is also directed to a method for inhibiting the metastasis of a mammalian tumor comprising, administering to a mammal suspected of having a metastatic tumor an effective amount of an antisense oligonucleotide from about 20 nucleotides to about 100 nucleotides complementary to the mammalian adult IGF-II mRNA selected from the group consisting of SEQ ID NOs:17–31 from Table 2 under conditions such that the metastasis of the tumor is inhibited.

BRIEF DESCRIPTION OF THE DRAWINGS

FIGS. 2A–D are graphs of the percentage of inhibition of the colony forming ability of different cell lines by administration of the indicated antisense oligonucleotides. FIG. 2A shows the percentage inhibition of the human rhabdomyosarcoma cell line RD; FIG. 2B shows percentage inhibition of the human prostate cancer cell line PC-3; FIG. 2C shows the percentage inhibition of the human pancreatic cancer cell line AsPC-1: FIG. 2D shows the percentage inhibition of the human neuroblastoma cell line SK-N-AS.

FIGS. 11(A–D) is part of the nucleotide sequence of the human IGF-II gene. FIG. 11A is the sequence of exon 4 [SEQ ID NO:34], FIG. 11B is the sequence of exon 5 [SEQ ID NO:35], FIG. 11C is the sequence of exon 6 [SEQ ID NO:36] and FIG. 11D is the sequence of exons 7–9 [SEQ ID NO:37].

DETAILED DESCRIPTION OF THE INVENTION

Figure 1:
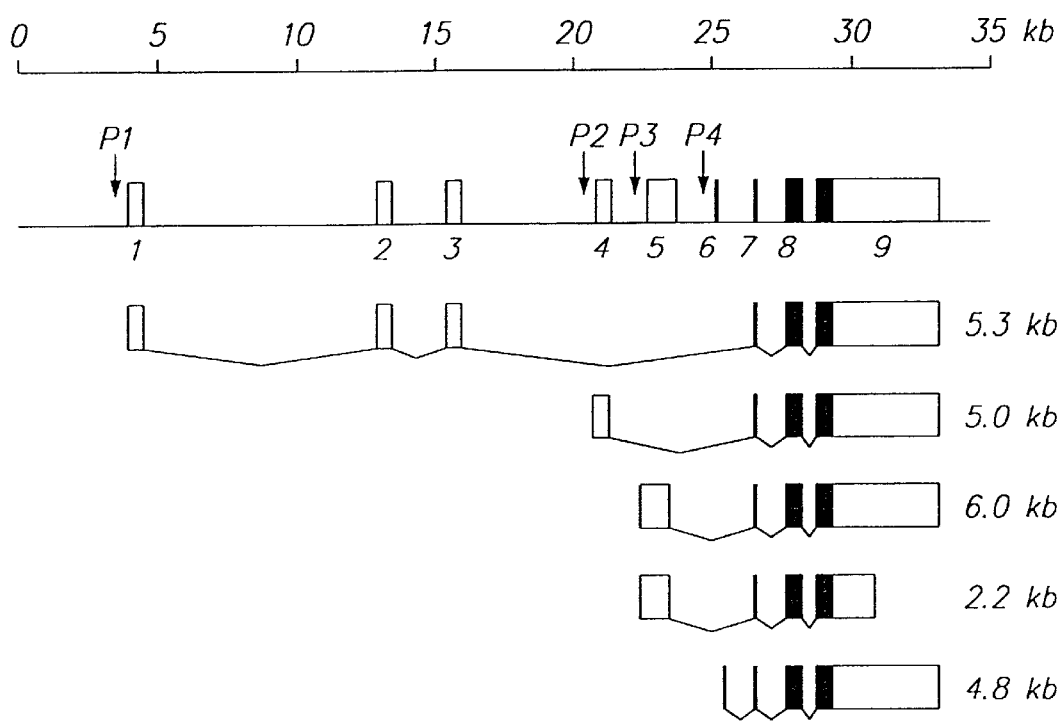
FIG. 1 is map of the human IGF-II gene and alternatively transcribed and spiced mRNAs. The numbered boxes (1–9) indicate the exons of IGF-II gene. Four promoters (P1–P4) are also indicated with arrows. Various IGF-II mRNA species are depicted in the lower part of the figure with their corresponding sizes. The solid boxes represent coding regions of the IGF-II precursor protein.

This invention relates to oligonucleotides that are complementary to mammalian IGF II genes which oligonucleotides modulate tumor cell growth in mammals. It appears that overexpression of IGF-II observed in various human primary cancers and cell lines results from reactivation (in liver) or overexpression (in other organs) of fetal mRNA species. Accordingly, antisense oligonucleotides designed to specifically target fetal transcripts in the 5'UTR, leaving adult transcripts intact, will be highly specific for targeting tumor cells.

Without being limited to a theory or mechanism, it is believed that these antisense compounds will exert their antitumor activity by not only suppressing autocrine growth of tumor cells and possibly inducing apoptosis, but also inhibiting autocrine/paracrine function of IGF-II, such as tumor cell motility and/or induction of endothelial cell migration and angiogenesis.

Definitions:

As used herein, the following terms have the following meanings:

The term "antisense oligonucleotide" as used herein means a nucleotide sequence that is complementary to the desired mRNA. The antisense oligonucleotide is complementary to any portion of a mammalian IGF-II mRNA that effectively acts as a target for inhibiting IGF-II expression. Preferably, the antisense oligonucleotide is complementary to the 5' untranslated region of the IGF-II fetal transcript. More preferably, the antisense oligonucleotide is complementary to the nucleotide sequence of exons 4, 5 or 6 as set forth in FIGS. 11A–C.

Without being limited to any theory or mechanism, it is generally believed that the activity of antisense oligonucleotides depends on the binding of the oligonucleotide to the target nucleic acid (e.g. to at least a portion of a genomic region, gene or mRNA transcript thereof), thus disrupting the function of the target, either by hybridization arrest or by destruction of target RNA by RNase H (the ability to activate RNase H when hybridized to RNA).

The term "oligonucleotide" refers to an oligomer or polymer of nucleotide or nucleoside monomers consisting of naturally occurring bases, sugars, and inter-sugar (backbone) linkages. The term also includes modified or substituted oligomers comprising non-naturally occurring monomers or portions thereof, which function similarly. Such modified or substituted oligomers may be preferred over naturally occurring forms because of the properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells) or two or more oligonucleotides of the invention may be joined to form a chimeric oligonucleotide.

The antisense oligonucleotides of the present invention may be ribonucleic or deoxyribonucleic acids and may contain naturally occurring or synthetic monomeric bases, including adenine, guanine, cytosine, thymine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other 8-substituted guanines, other aza and deaza uracils, thymidines, cytosines or guanines, 5-trifluoromethyl uracil and 5-trifluoro cytosine. The modifications may also include attachment of other chemical groups such as methyl, ethyl, propyl groups to the various parts of the oligonucleotides including the sugar, base or backbone components.

The antisense oligonucleotides of the invention may also comprise modified phosphorus oxygen heteroatoms in the phosphate backbone, short chain alkyl or cycloalkyl inter-sugar linkages or short chain heteroatom or heterocyclic intersugar linkages. For example, the antisense oligonucleotides may contain methyl phosphonates, phosphorothioates, phosphorodithioates, phosphotriesters, and morpholino oligomers. The antisense oligonucleotides may comprise phosphorothioate bonds linking between the four to six 3'-terminus nucleotides. The phosphorothioate bonds may link all the nucleotides. The phosphorothioate linkages may be mixed $R_P$ and $S_P$ enantiomers, or they may be stereoregular or substantially stereoregular in either $R_P$ or $S_P$ form.

The antisense oligonucleotides may also have sugar mimetics. The oligonucleotide may have at least one nucleotide with a modified base and/or sugar, such as a 2'-O-substituted ribonucleotide. For purposes of the invention, the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups. The oligonucleotides of the invention may include four or five ribonucleotides 2'-O-alkylated at their 5' terminus and/or four or five ribonucleotides 2'-O-alylated at their 3' terminus.

The antisense oligonucleotides of the invention may also comprise nucleotide analogues wherein the structure of the nucleotide is fundamentally altered. An example of such an oligonucleotide analogue is a peptide nucleic acid (PNA) wherein the deoxyribose (or ribose) phosphate backbone in DNA (or RNA) is replaced with a polyamide backbone which is similar to that found in peptides (Nielsen et al.[29]; Good and Nielsen[30]; Buchardt, deceased, et al.[31], U.S. Pat. No. 5,766,855; Buchardt, deceased, et al.[32], U.S. Pat. No. 5,719,262). PNA analogues have been shown to be resistant to degradation by enzymes and to have extended lives in vivo and in vitro. PNAs also bind more strongly to a complementary DNA sequence than to a naturally occurring nucleic acid molecule due to the lack of charge repulsion between the PNA strand and the DNA strand.

The oligonucleotides of the present invention may also include other nucleotides comprising polymer backbones, cyclic backbones, or acyclic backbones. For example, the nucleotides may comprise morpholino backbone structures (U.S. Pat. No. 5,034,506 (33)).

The oligonucleotides of the present invention are "nuclease resistant" when they have either been modified such that they are not susceptible to degradation by DNA and RNA nucleases or alternatively they have been placed in a delivery vehicle which in itself protects the oligonucleotide from DNA or RNA nucleases. Nuclease resistant oligonucleotides include, for example, methyl phosphonates, phosphorothioates, phosphorodithioates, phosphotriesters, and morpholino oligomers. Suitable delivery vehicles for conferring nuclease resistance include, for example liposomes.

The oligonucleotides of the present invention may also contain groups, such as groups for improving the pharmacokinetic properties of an oligonucleotide, or groups for improving the pharmacodynamic properties of an oligonucleotide.

The antisense oligonucleotides are preferably selected from the sequence complementary to the IGF-II gene such that the sequence exhibits the least likelihood of showing duplex formation, hair-pin formation, and homooligomer/sequence repeats but has a high to moderate potential to bind to the IGF-II gene sequences. These properties may be determined using the computer modeling program OLIGO Primer Analysis Software, Version 5.0 (distributed by National Biosciences, Inc., Plymouth, Minn.). This computer program allows the determination of a qualitative estimation of these five parameters.

Alternatively, the antisense oligonucleotides may also be selected on the basis that the sequence is highly conserved for the IGF-II gene between two or more mammalian species. These properties may be determined using the BLASTN program (Altschul, et al. (34)) of the University of Wisconsin Computer group (GCG) software (Devereux J. et al. (35)) with the National Center for Biotechnology Information (NCBI) databases.

The antisense oligonucleotides may include mutations, such as substitutions, insertions and deletions. Preferably there will be less that 10% of the sequence having mutations.

The antisense oligonucleotides generally comprise from at least about 3 nucleotides or nucleotide analogs, more preferably they are at least about 5 nucleotides, more preferably they are at least about 7 nucleotides, more preferably they are at least about 9 nucleotides and most preferably they are at least about 20 nucleotides. The antisense oligonucleotides are preferably less than about 100 nucleotides or nucleotide analogs, more preferably, less than about 50 nucleotides or nucleotide analogs, most preferably less than about 35 nucleotide or nucleotide analogs.

Preferably, the antisense oligonucleotides are complementary to the 5' untranslated region of the fetal IGF-II transcript. The "untranslated region of the fetal IGF-II transcript" means that part of the IGf-II gene which is transcribed in fetal cells to form the major IGF-II transcript and which does not form part of the adult IGF-II transcript (the major transcript in adult cells). Preferably the "untranslated region of the fetal IGF-II transcript" is exons 4, 5 and 6 of the IGF-II gene. Most preferably, the "untranslated region of the fetal IGF-II transcript" is that substantially the sequence of exons 4, 5 and 6 as set forth in FIGS. 11A–C.

Preferably, the antisense oligonucleotides comprise the sequences set forth in Tables 1 and 2 (below).

TABLE 1

Antisense Sequences designed to target human IGF-II Fetal mRNA

| SEQ ID NO. | Name | Sequence 5'-3' | Tm (° C.) | ΔG (kcal/mol) |
|---|---|---|---|---|
| 1 | GTI4001 | GGC TCG CTG GGG CAG GAG GA | 74.6 | −46.5 |
| 2 | GTI4002 | GCT GGT GGG CAG AGC GCG GG | 78.0 | −48.5 |
| 3 | GTI4003 | TTG GTG TCT ACA GCT CAG CA | 57.8 | −35.2 |
| 4 | GTI4004 | CAG CGA GGC AGC GGG CGG CG | 82.7 | −52.5 |
| 5 | GTI4005 | TCG GGC GAA GCG GGG ATG GG | 79.0 | −50.4 |
| 6 | GTI4006 | CGG GCC TCG GGA GGG GGA CA | 78.2 | −49.4 |
| 7 | GTI4007 | GAC CGC GGG CGC CCA GCT CG | 81.7 | −51.9 |
| 8 | GTI4008 | ACG TCG AGG GGC CGG GGG AG | 77.4 | −49.3 |
| 9 | GTI4009 | CGG GAG AAA GAG CGG GGG CC | 75.1 | −48.5 |
| 10 | GTI4010 | CGA GAG GGC GGG CGT GAG GG | 77.0 | −48.4 |
| 11 | GTI4011 | CAG CGA GAG GCG GGC AGG CG | 78.2 | −49.0 |
| 12 | GTI4012 | CGG GCT GTC TTC GGG CTG GG | 74.9 | −47.0 |
| 13 | GTI4013 | GCG ACG GGG CAG AGC GGG GG | 80.7 | −51.4 |
| 14 | GTI4014 | CGC TGC CGC CCA CCT CCC TG | 77.8 | −48.5 |
| 15 | GTI4015 | TTG GTG TCT GGA AGC CGG CG | 72.0 | −44.3 |

The antisense oligonucleotides were selected from the sequence complementary to the human IGF-II mRNA such that the sequence exhibits the least likelihood of showing duplex formation, hairpin formation, and homooligomers/sequence repeats but has a high potential to bind to the IGF-II mRNA sequence and contains a GC clamp. In addition, false priming to other frequently occurring or repetitive sequences in human and mouse was eliminated. These properties were determined using the computer modeling program OLIGO® Primer Analysis Software, Version 5.0 (distributed by National Biosciences, Inc., Plymouth, Minn.).

TABLE 2

Antisense oligonucleotides having a sequence complementary to all regions of the human IGF-II mRNA

| SEQ ID NO. | Name | Sequence 5'-3' | Tm (° C.) | ΔG (kcal/mol) |
|---|---|---|---|---|
| 16 | GTI4016 | TTC CCC ATT GGG ATT CCC AT | 66.8 | −42.4 |
| 17 | GTI4017 | GTC CAC CAG CTC CCC GCC GC | 76.9 | −47.9 |
| 18 | GTI4018 | CGA TGC CAC GGC TGC GAC GG | 77.6 | −47.6 |
| 19 | GTI4019 | ACG CAG GAG GGC AGG CAG GC | 74.7 | −46.5 |
| 20 | GTI4020 | GCG AGC ACG TGA CCC CGG CG | 78.7 | −48.6 |
| 21 | GTI4021 | CGT GGG CGG GGT CTT GGG TG | 75.4 | −46.7 |
| 22 | GTI4022 | TGT TTC GGG GAG GCG GGG CA | 77.5 | −48.8 |
| 23 | GTI4023 | GCG GTA CGA GCG ACG TGC CC | 73.8 | −45.9 |
| 24 | GTI4024 | CAA ATG CCG CCG GCC GCA CA | 79.7 | −49.8 |
| 25 | GTI4025 | CGC ATC AGT GCA CGG CCC CC | 76.5 | −46.9 |
| 26 | GTI4026 | GTG CGG AAG GCG GCC ACC CT | 76.4 | −48.2 |
| 27 | GTI4027 | CAG GGT GCT GAG GGG CGG GC | 76.9 | −48.0 |
| 28 | GTI4028 | GCT CCG GGG CCC AAG CAA CC | 75.9 | −48.3 |
| 29 | GTI4029 | CCC TAG GCG CCG CGG TGG TG | 77.6 | −49.3 |
| 30 | GTI4030 | TGG CAT GGA CGA CCC CCG GG | 77.7 | −48.1 |
| 31 | GTI4031 | GGG CCG CAA GGT GGA CCG AG | 74.8 | −46.7 |

The antisense oligonucleotides were selected from the sequence complementary to the human IGF-II mRNA such that the sequence exhibits the least likelihood of showing duplex formation, hairpin formation, and homooligomers/sequence repeats but has a high potential to bind to the IGF-II mRNA sequence and contains a GC clamp. In addition, false priming to other frequently occurring or repetitive sequences in human and mouse was eliminated. These properties were determined using the computer modeling program OLIGO® Primer Analysis Software, Version 5.0 (distributed by National Biosciences, Inc., Plymouth, Minn.).

In Tables 1 and 2 the "Tm" is the melting temperature of an oligonucleotide duplex calculated according to the nearest-neighbour thermodynamic values. At this temperature 50% of nucleic acid molecules are in duplex and 50% are denatured. The "ΔG" is the free energy of the oligonucleotide, which is a measurement of an oligonucleotide duplex stability.

The term "alkyl" refers to monovalent alkyl groups preferably having from 1 to 20 carbon atoms and more preferably 1 to 6 carbon atoms. This term is exemplified by groups such as methyl, ethyl, n-propyl, iso-propyl, n-butyl, iso-butyl, n-hexyl, and the like.

The term "aryl" refers to an unsaturated aromatic carbocyclic group of from 6 to 14 carbon atoms having a single ring (e.g., phenyl) or multiple condensed (fused) rings (e.g., naphthyl or anthryl). Preferred aryls include phenyl, naphthyl and the like.

The term "halo" or "halogen" refers to fluoro, chloro, bromo and iodo and preferably is either fluoro or chloro.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "pharmaceutically acceptable" means a non-toxic material that does not interfere with the effectiveness of the biological activity of the active ingredient(s). The material is compatible with a biological system such as a cell, cell culture, tissue or organism.

The term "pharmaceutically acceptable salt" refers to salts which retain the biological effectiveness and properties of the antisense oligonucleotides of this invention and which are not biologically or otherwise undesirable. In many cases, the antisense oligonucleotides of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethylamine, diethylamine, tri(isopropyl)amine, tri(n-propyl)amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "IGF-II gene" or "insulin-like growth factor II" refers to any gene which encodes a protein that is capable of binding to the IGF-I or IGF-II receptor. Preferably the IGF-II gene has one or more regions with a nucleotide sequence substantially similar to the sequences of exons 4, 5, 6 or 7–9 as set forth in FIGS. 11A–D.

The term "complementary to" means that the antisense oligonucleotide sequence is capable of binding to the target sequence, i.e. the IGF-II gene (or mRNA). Preferably, the antisense oligonucleotide binds to the nucleic acid sequence under physiological conditions, e.g. by Watson-Crick base pairing (interaction between oligonucleotide and single-stranded nucleic acid) or by Hoogsteen base pairing (interaction between oligonucleotide and double-stranded nucleic acid) or by any other means including in the case of an oligonucleotide binding to RNA, causing pseudoknot formation. Binding by Watson-Crick or Hoogsteen base pairing under physiological conditions is measured as a practical matter by observing interference with the function of the nucleic acid sequence.

Preferably the antisense oligonucleotide sequence has at least about 75% identity with the target sequence, preferably at least about 90% identity and most preferably at least about 95% identity with the target sequence allowing for gaps or mismatches of several bases. Identity can be determined, for example, by using the BLASTN program of the University of Wisconsin Computer Group (GCG) software. Preferably the antisense oligonucleotide sequence hybridizes to the IGF-II mRNA with a melting temperature of at least 45° C., more preferably at least about 50° C. and most preferably at least about 55° C. as determined by the OLIGO Primer Analysis Software, version 5.0 program described herein.

The term "inhibiting growth" means a reduction or inhibition in the growth of at least one tumor cell type, preferably by at least 10%, more preferably of at least 50% and most preferably of at least 75%. The inhibition of growth of tumors can be determined by measuring the size of the tumor in nude mice or the inability of the tumor cells to form colonies in vitro.

The term "inhibiting metastasis" means reducing or inhibiting the number of metastatic tumors that develop, preferably by at least 10% and more preferably by at least 50%. This can be determined by the methods set forth in the Examples and other methods known in the art.

The term "inhibiting expression of IGF-II" means that the antisense oligonucleotide reduces the level of IGF-II mRNA or the level of IGF-II protein produced by the cell when the oligonucleotide is administered to the cell.

The term "mammal" or "mammalian" means all mammals including humans, ovines, bovines, equines, swine, canines, felines and mice, etc., preferably it means humans.

A "mammal suspected of having a tumor" means that the mammal may have a proliferative disorder or tumor or has been diagnosed with a proliferative disorder or tumor or has been previously diagnosed with a proliferative disorder or tumor, the tumor has been surgically removed and the mammal is suspected of harboring some residual tumor cells.

Preparation of the Antisense Oligonucleotides

The antisense oligonucleotides of the present invention may be prepared by conventional and well-known techniques. For example, the oligonucleotides may be prepared using solid-phase synthesis and in particular using commercially available equipment such as the equipment available from Applied Biosystems Canada Inc., Mississauga, Canada. The oligonucleotides may also be prepared by enzymatic digestion of the naturally occurring IGF-II gene by methods known in the art.

These oligonucleotides can be prepared by the art recognized methods such as phosphoramidate or H-phosphoate chemistry which can be carried out manually or by an automated synthesizer as described by Uhlmann et al. (21) and Agrawal et al. (22).

Isolation and Purification of the Antisense Oligonucleotides

Isolation and purification of the antisense oligonucleotides described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. However, other equivalent separation or isolation procedures could, of course, also be used.

An expression vector comprising the antisense oligonucleotide sequence may be constructed having regard to the sequence of the oligonucleotide and using procedures known in the art.

Vectors can be constructed by those skilled in the art to contain all the expression elements required to achieve the desired transcription of the antisense oligonucleotide sequences. Therefore, the invention provides vectors comprising a transcription control sequence operatively linked to a sequence which encodes an antisense oligonucleotide. Suitable transcription and translation elements may be derived from a variety of sources, including bacterial, fungal, viral, mammalian or insect genes. Selection of appropriate elements is dependent on the host cell chosen.

Reporter genes may be included in the vector. Suitable reporter genes include β-galactosidase (e.g. lacZ), chloramphenicol, acetyl-ransferase, firefly luciferase, or an immunoglobulin or portion thereof. Transcription of the antisense oligonucleotide may be monitored by monitoring for the expression of the reporter gene.

The vectors can be introduced into cells or tissues by any one of a variety of known methods within the art. Such methods can be found generally described in Sambrook et al.[24]; Ausubel et al.[25]; Chang et al.[36]; Vega et al.[37]; and Vectors: A Survey of Molecular Cloning Vectors and Their Uses[38] and include, for example, stable or transient transfection, lipofection, electroporation and infection with recombinant viral vectors.

Introduction of nucleic acids by infection offers several advantages. Higher efficiency and specificity for tissue type can be obtained. Viruses typically infect and propagate in specific cell types. Thus, the virus' specificity may be used to target the vector to specific cell types in vivo or within a tissue or mixed culture of cells. Viral vectors can also be modified with specific receptors or ligands to alter target specificity through receptor mediated events.

It is contemplated that the oligonucleotide of this invention may be a ribozyme which cleaves the mRNA. The ribozyme preferably has a sequence homologous to a sequence of an oligonucleotide of the invention and the necessary catalytic center for cleaving the mRNA. For example, a homologous ribozyme sequence may be selected which destroys the IGF-II mRNA. The ribozyme type utilized in the present invention may be selected from types known in the art. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan 1994, U.S. Pat. No. 5,225,347[3]). Hammerhead and hairpin ribozyme motifs are most commonly adapted for trans cleavage of mRNAs for gene therapy (Sullivan 1994). Hairpin ribozymes are preferably used in the present invention. In general, the ribozyme is from 30 to 100 nucleotides in length.

The oligonucleotides of the invention may be insolubilized. For example, the oligonucleotide may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk etc. The carrier may in the shape of, for example, a tube, test plate, beads disc, sphere etc.

The insoubilized oligonucleotide may be prepared by reacting the material with the suitable insoluble carrier using known chemical or physical methods, for example, cyanogen bromide coupling.

Pharmaceutical Formulations

When employed as pharmaceuticals, the antisense oligonucleotides are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound. The pharmaceutical composition is, for example, administered intravenously. It is contemplated that the pharmaceutical composition may be administered directly into the tumor to be treated.

This invention also includes pharmaceutical compositions which contain, as the active ingredient, one or more of the antisense oligonucleotides associated with pharmaceutically acceptable carriers or excipients. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 1% to about 95%, more usually about 5% to about 90% of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The antisense oligonucleotide is effective over a wide dosage range and is generally administered in a pharmaceutically effective amount. An effective amount is that amount which when administered alleviates the symptoms. Preferably the effective amount is that amount able to inhibit tumor cell growth. Preferably the effective amount is from about 0.1 mg/kg body weight to about 20 mg/kg body weight. It will be understood, however, that the amount of the antisense oligonucleotide actually administered will be determined by a physician, in the light of the relevant circumstances, including the condition to be treated, the chosen route of administration, the actual compound administered, the age, weight, and response of the individual patient, the severity of the patient's symptoms, and the like. The course of therapy may last from several days to several months or until diminution of the disease is achieved. The antisense oligonucleotide may be administered in combination with other known therapies.

When co-administered with one or more other therapies, the oligonucleotide may be administered either simultaneously with the other treatments(s), or sequentially. If administered sequentially, the attending physician will decide on the appropriate sequence of administering the oligonucleotide in combination with the other therapy.

For preparing solid compositions such as tablets, the principal active ingredient/antisense oligonucleotide is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The pharmaceutical composition of the invention may be in the form of a liposome, in which the oligonucleotide is combined, in addition to other pharmaceutically acceptable carriers, with amphipathic agents such as lipids which exist in aggregated form as micells, insoluble monolayers, liquid crystals or lamellar layers which are in aqueous solution. Suitable lipids for liposomal formulation include, without limitation, monoglycerides, diglycerides, sulfatides, lysolecithin, phospholipids, saponin, bile acids and the like. One particularly useful lipid carrier is lipofectin. Preparation of such liposomal formulations is within the skill in the art, for example, International Patent No. WO97/21808 (28) The pharmaceutical composition may further include compounds such as cyclodextrins and the like which enhance delivery of oligonucleotides into cells or slow release polymers.

Another preferred formulation employed in the methods of the present invention employs transdermal delivery devices ("patches"). Such transdermal patches may be used to provide continuous or discontinuous infusion of the antisense oligonucleotides of the present invention in controlled amounts. The construction and use of transdermal patches for the delivery of pharmaceutical agents is well known in the art. See, for example, U.S. Pat. No. 5,023,252[40], herein incorporated by reference. Such patches may be constructed for continuous, pulsatile, or on demand delivery of pharmaceutical agents.

Another preferred method of delivery involves "shotgun" delivery of the naked antisense oligonucleotides across the dermal layer. The delivery of "naked" antisense oligonucleotides is well known in the art. See, for example, Felgner et al., U.S. Pat. No. 5,580,859[41]. It is contemplated that the antisense oligonucleotides may be packaged in a lipid vesicle before "shotgun" delivery of the antisense oligonucleotide.

The following formulation examples illustrate representative pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

Formulation Example 9

A formulation may be prepared as follows:

| Ingredient | Quantity |
|---|---|
| Active Ingredient | 5.0 mg |
| Corn Oil | 1.0 mL |

Formulation Example 10

A topical formulation may be prepared as follows:

| Ingredient | Quantity |
|---|---|
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Other suitable formulations for use in the present invention can be found in *Remington's Pharmaceutical Sciences* (23).

The antisense oligonucleotides or the pharmaceutical composition comprising the antisense oligonucleotides may be packaged into convenient kits providing the necessary materials packaged into suitable containers.

The antisense oligonucleotides of the invention in the form of a therapeutic formulation are useful in treating diseases, and disorders and conditions associated with tumor growth. In such methods a therapeutic amount of a oligonucleotide effective in inhibiting the expression of fetal transcripts of IGF-II is administered to a cell. This cell may be part of a cell culture, a tissue culture, or may be part of the whole body of a mammal such as a human.

The oligonucleotides and ribozymes of the invention modulate tumor cell growth. Therefore methods are provided for interfering or inhibiting tumor cell growth in a mammal comprising contacting the tumor or tumor cells with an antisense oligonucleotide of the present invention.

The term "contact" refers to the addition of an oligonucleotide, ribozyme, etc. to a cell suspension or tissue sample or administering the oligonucleotides etc. directly or indirectly to cells or tissues within an animal.

The methods may be used to treat proliferative disorders including various forms of cancer or tumors such a leukemias, lymphomas (Hodgkins and non-Hodgkins), sarcomas, melanomas, adenomas, carcinomas of solid tissue, hypoxic tumors, squamous cell carcinomas of the mouth, throat, larynx and lung, genitourinary cancers such as cervical and bladder cancer, hematopoietic cancers, colon cancer, breast cancer, pancreatic cancer, renal cancer, brain cancer, skin cancer, liver cancer, head and neck cancers, and nervous system cancers, as well as benign lesions such as papillomas. Other proliferative disorders such as psoriasis and those involving arthrosclerosis are also included.

The oligonucleotides of the invention may also be used to treat drug resistant tumors. Examples of drug resistant tumors are tumors resistant to such chemotherapeutic agents as 5-fluorouracil, mitomycin C, methotrexate or hydroxyurea and tumors expressing high levels of P-glycoprotein which is known to confer resistance to multiple anticancer drugs such as colchicine, vinblastine and doxorubicin; or tumors expressing multi-drug resistance protein as described by Dreeley et al. (28). Accordingly, it is contemplated that the oligonucleotides of the present invention may be administered in conjunction with or in addition to known anticancer compounds or chemotherapeutic agents. Chemotherapeutic agents are compounds which may inhibit the growth of tumors. Such agents, include, but are not limited to, 5-fluorouracil, mitomycin C, methotrexate and hydroxyurea. It is contemplated that the amount of chemotherapeutic agent may be either an effective amount, i.e. an amount sufficient to inhibit tumor growth or a less than effective amount.

The oligonucleotides of the present invention have been found to reduce the growth of tumors that are metastatic such as C8161 melanoma cells. In an embodiment of the invention, a method is provided for reducing the growth of metastastic tumors in a mammal comprising administering an effective amount of an oligonucleotide from about 3 to about 100 nucleotides, comprising a sequence complementary to the 5' untranslated region of mammalian fetal IGF-II mRNA. The sequence may be selected from the group of oligonucleotides shown in Table 1. In another embodiment, a method is provided for reducing the growth of metastastic tumors in a mammal comprising administering an effective amount of an oligonucleotide from about 20 to about 100 nucleotides, comprising a sequence selected from the group of SEQ ID NO: 17–31 set forth in Table 2.

The oligonucleotides may be delivered using viral or non-viral vectors. Sequences may be incorporated into cassettes or constructs such that an oligonucleotide of the invention is expressed in a cell. Preferably, the construct contains the proper transcriptional control region to allow the oligonucleotide to be transcribed in the cell.

Therefore, the invention provides vectors comprising a transcription control sequence operatively linked to a sequence which encodes an oligonucleotide of the invention. The present invention further provides host cells, selected from suitable eucaryotic and procaryotic cells, which are transformed with these vectors.

Suitable vectors are known and preferably contain all of the expression elements necessary to achieve the desired transcription of the sequences. Phagemids are a specific example of such beneficial vectors because they can be used either as plasmids or as bacteriophage vectors. Examples of the vectors include viruses such as bacteriophages, baculoviruses, retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into the cells by stable or transient transfection, lipofection, electroporation and infection with recombinant viral vectors.

Additional features can be added to the vector to ensure its safety and/or enhance its therapeutic efficacy. Such features include, for example, markers that can be used to negatively select against cells infected with recombinant viruses. An example of such a negative selection marker is the TK gene which confers sensitivity to the antiviral gancyclovir. Features that limit expression to particular cell types can also be included. Such features include, for example, promoter and regulatory elements that are specific for the desired cell type.

Retroviral vectors are another example of vectors useful for the in vivo introduction of a desired nucleic acid because they offer advantages such as lateral infection and targeting specificity. Lateral infection is the process by which a single infected cell produces many progeny virions that infect neighboring cells. The result is that a large area becomes rapidly infected.

A vector to be used in the methods of the invention may be selected depending on the desired cell type to be targeted. For example, if breast cancer is to be treated, then a vector specific for epithelial cell may be used. Similarly, if cells of the hematopoietic system are to be treated, then a viral vector that is specific for blood cells is preferred.

Utility

The antisense oligonucleotides of the present invention may be used for a variety of purposes. They may be used to inhibit the expression of the IGF-II gene in a mammalian cell, resulting in the inhibition of growth of that cell. The oligonucleotides may be used as hybridization probes to detect the presence of the IGF-II mRNA in mammalian cells. When so used the oligonucleotides may be labeled with a suitable detectable group (such as a radioisotope, a ligand, another member of a specific binding pair, for example, biotin). Finally, the oligonucleotides may be used as molecular weight markers.

In order to further illustrate the present invention and advantages thereof, the following specific examples are given but are not meant to limit the scope of the claims in any way.

EXAMPLES

In the examples below, all temperatures are in degrees Celsius (unless otherwise indicated) and all percentages are weight percentages (also unless otherwise indicated).

In the examples below, the following abbreviations have the following meanings. If an abbreviation is not defined, it has its generally accepted meaning:
AS=antisense
cDNA=complementary deoxyribonucleic acid
ODN=oligodeoxynucleotide
μM=micromolar
mM=millimolar
M=molar
ml=milliliter
μl=microliter
mg=milligram
μg=microgram
PAGE=polyacrylamide gel electrophoresis
rpm=revolutions per minute
ΔG=free energy, a measurement of oligonucleotide duplex stability
kcal=kilocalories
FBS=fetal bovine serum
DTT=dithiothrietol
SDS=sodium dodecyl sulfate
PBS=phosphate buffered saline
PMSF=phenylmethylsulfonyl fluoride
GAPDH=glyceraldehyde-3-phosphate dehydrogenase
IgG=immunoglobulin G
kDa=kilodalton
PCR=polymerase chain reaction
Tris-HCl=Tris(hydroxymethyl)aminomethane-hydrochloric acid
TRIzol=total RNA isolation reagent
ECL=western blotting detection reagents
IGF-I insulin-like growth factor I
IGF-II=insulin-like growth factor II
UTR=untranslated region General Methods in Molecular Biology:

Standard molecular biology techniques known in the art and not specifically described were generally followed as in Sambrook et al.[24]; Ausubel et al.[25]; and Perbal[26].

Oligonucleotides

The antisense oligonucleotides were selected from the sequence complementary to the IGF-II mRNA such that the sequence exhibits the least likelihood of showing duplex formation, hairpin formation, and homooligomers/sequence repeats but has a high potential to bind to the IGF-II mRNA sequence. In addition, a false priming to other frequently occurring or repetitive sequences in human and mouse was eliminated. These properties were determined using the computer modeling program OLIGO® Primer Analysis Software, Version 5.0 International Biosciences, Inc. Plymouth Minn.). Based on this analysis, phosphorothioate antisense oligonucleotides were designed and then made by methods well known in the art.

Cell Lines

Five different human cancer cell lines including embryonal rhabdomyosarcoma (RD), neuroblastoma (SK-N-AS), Wilms' tumor (G401), melanoma (C8161), human prostate adenocarcinoma (PC-3), metastatic pancreatic adenocarcinoma (AsPC-1) were obtained from American Type Culture Collection (ATCC). The cell lines were maintained in α-MEM medium (Gibco BRL, Gaithersburg, Md.) supplemented with 10% fetal bovine serum (FBS).

Example 1

The Inhibition of Growth of Cancer Cell Lines by Antisense Oligonucleotides Complementary to IGF-II The colony forming ability of cancer cell lines treated with different phosphorothioate antisense oligonucleotides was estimated using a method previously described (Choy et al.[18]). Specifically, aliquots of a tumor cell suspension were seeded into 60 mm tissue culture dishes at a density of approximately $1 \times 10^4$ and incubated overnight at 37° C. in α-MEM medium supplemented with 10% FBS. Cells were washed once in 5 ml of PBS and treated with 0.2 μM of the indicated antisense oligonucleotides in the presence of cationic lipid (Lipofectin reagent, final concentration, 5 μg/ml, Gibco-BRL, Gaithersburg, Md.) for 4 hours. The antisense oligonucleotides were removed by washing the cells once with PBS and the cells were cultured in growth medium (α-MEM medium supplemented with 10% FBS) for 7 to 10 days at 37° C. Colonies were stained with methylene blue and scored by direct counting as described (Choy et al.18 and Huang and Wright[20]). Percent inhibition was calculated by comparison with the number of colonies present in cultures grown in the absence of antisense oligonucleotides. All experiments were performed in quadruplicate.

Figure 2A:
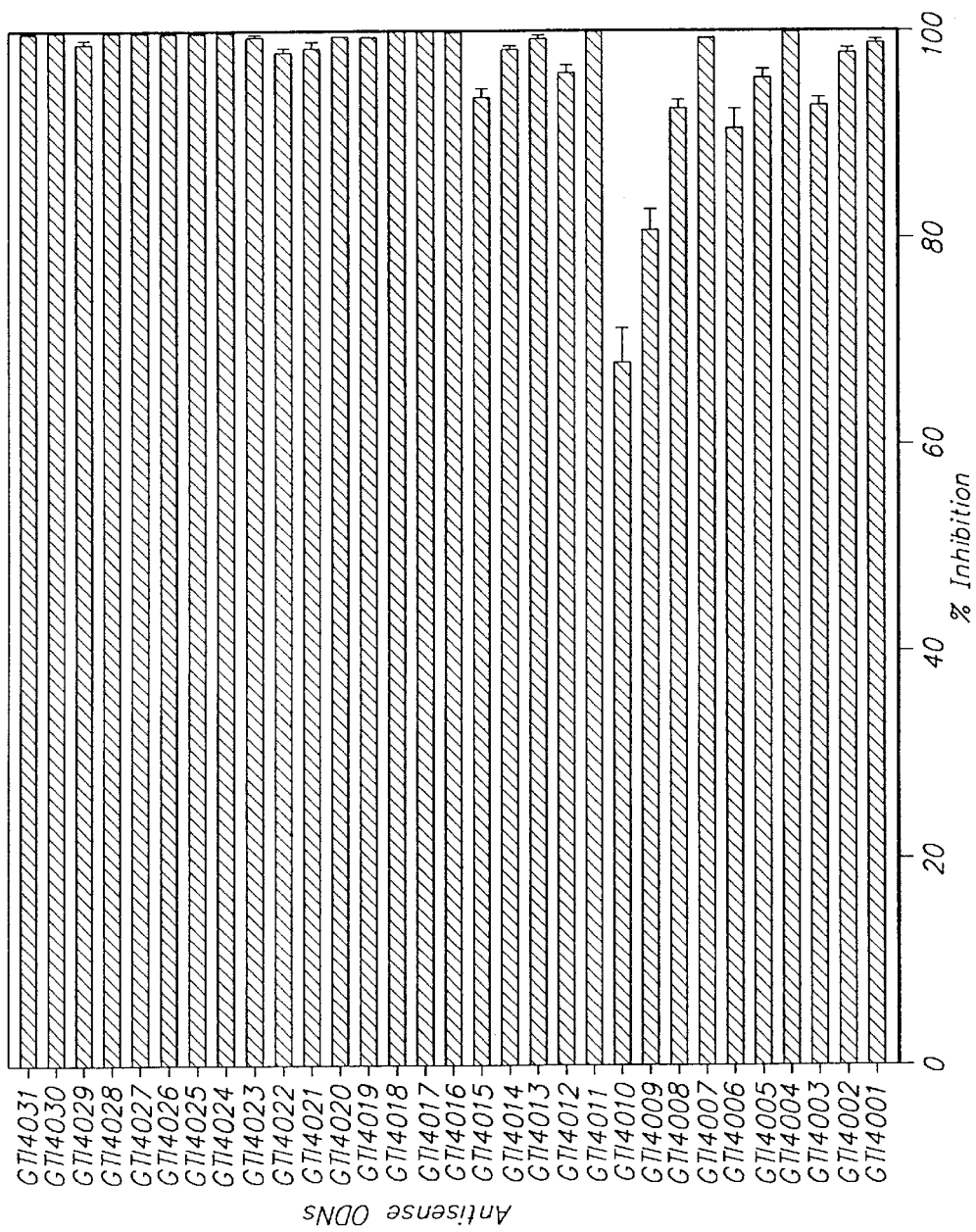
Figure 2C:
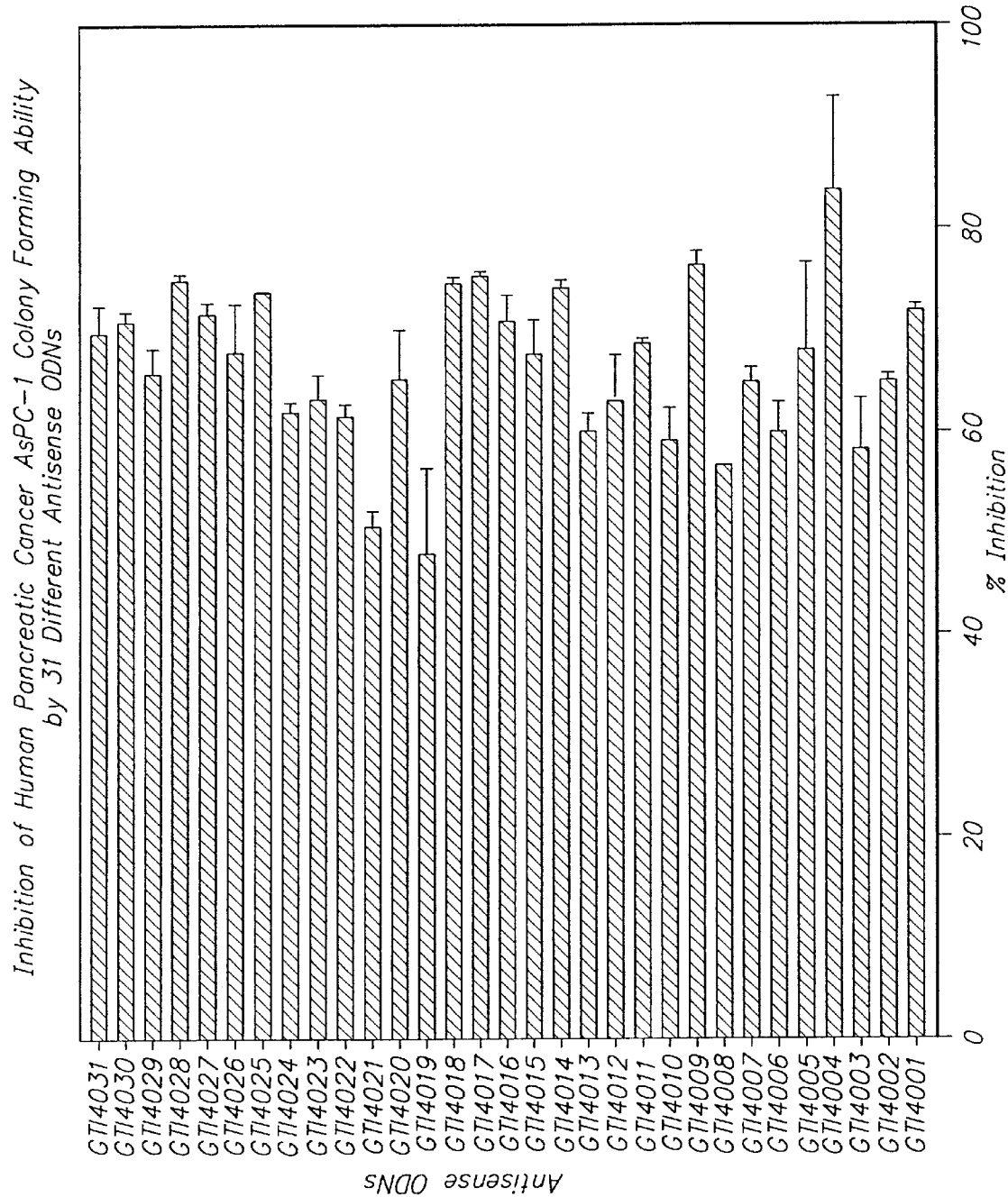
Figure 2D:
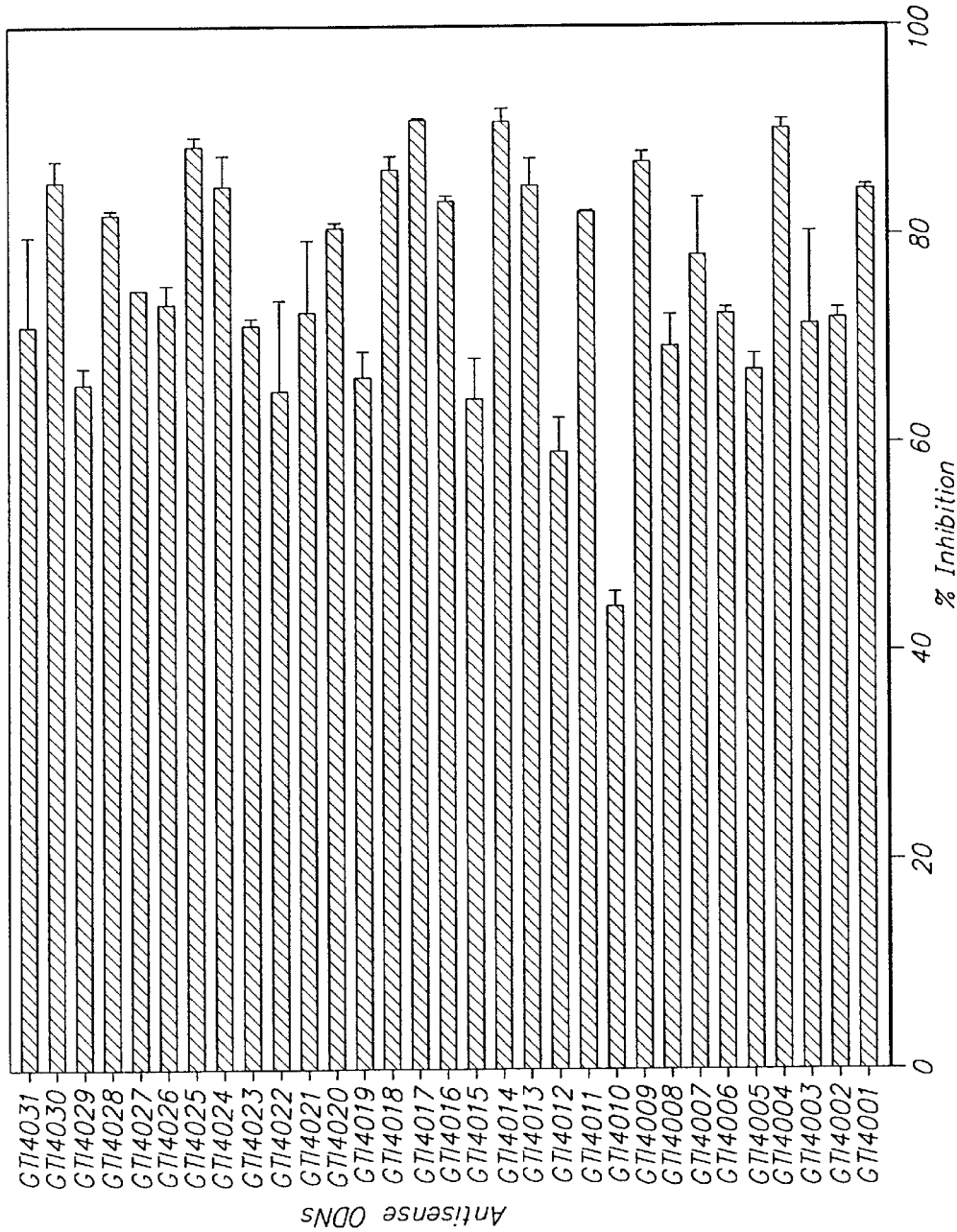

The antisense oligonucleotides exerted inhibitory effects on the colony forming ability of the human tumor cell lines. The percent inhibition of each antisense oligonucleotide is shown in FIG. 2A for rhabdomyosarcoma (RD); FIG. 2B for human prostate cancer cell line (PC-3); FIG. 2C for human pancreatic cancer cell line (AsPC-1); and FIG. 2D for human neuroblastoma cell line (SK-N-AS).

Example 2

Decreased mRNA Levels Following Treatment with Antisense Oligonucleotides Complementary to IGF-II Human neuroblastoma cells (SK-N-AS) or rhabdomyosarcoma cells (RD) were grown to subconfluency (70–80%) and were treated with 0.2 μM of phosphorothioate antisense oligonucleotides complementary to IGF-II for 4 hours in the presence of cationic lipid (Lipofectin reagent, final concentration, 5 μg/ml, Gibco-BRL) and Opti-MEM (Gibco-BRL). Cells were washed once with PBS and incubated for 16 hours in α-MEM medium (Gibco-BRL) containing 10% FBS. Total RNA was prepared in TRizol reagent (Gibco-BRL) and Northern blot analysis was performed as described in Hurta and Wright(27) with some modifications. The blots were hybridized with $^{32}$P-labeled 389 bp PCR fragments synthesized using forward primer (5'-TAC CGC CCC AGT GAG ACC CT-3') [SEQ ID NO:32], reverse primer (5'-TGA CGT TTG GCC TCC CTG AA-3') [SEQ ID NO:33] and the human colorectal adenocarcinoma 5'-stretch plus cDNA library (Clonetech, Palo Alto Calif.) as a template. Human IGF-II mRNA was expressed as a ~6 kb nucleotide transcript (Werner et al.[6]). Equal RNA loading was demonstrated by methylene blue staining of the blot prior to hybridization.

Figure 3:
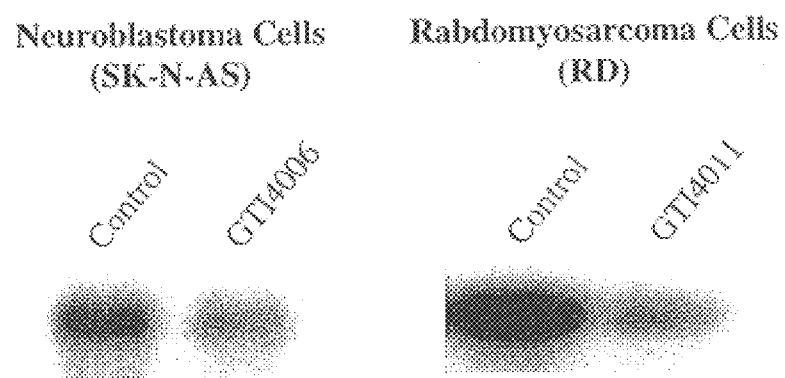
FIG. 3 is an autoradiograph of Northern Blots of RNA from either human neuroblastoma cell line SK-N-AS or rhabdomyosarcoma cell line (RD) after administration with antisense oligonucleotides: GTI4006 [SEQ ID NO:6] or GTI4011 [SEQ ID NO:11].

FIG. 3 shows that the antisense oligonucleotides reduce the IGF-II mRNA levels to at least 50% of the control cells.

Example 3

Decreased IGF-II Protein Levels Following Treatment with Antisense Oligonucleotides Complementary to IGF-II Human neuroblastoma cells (SK-N-AS) or rhabdomyosarcoma cells (RD) were grown to subconfluency (70–80%) and were treated with 0.2 μM of phosphorothioate antisense oligonucleotides complementary to IGF-II for 4 hours in the presence of cationic lipid (Lipofectin reagent, final concentration, 5 μg/ml, Gibco-BRL) and Opti-MEM (Gibco-BRL). Cells were washed once with PBS and incubated for 20 hours in α-MEM medium (Gibco-BRL) containing 10% FBS. The treatments and incubations were repeated once more before the whole cell protein extracts were prepared in 2×sample loading buffer (100 mM Tris-HCl, pH 6.8, 0.2 M DTT, 4% SDS, 20% glycerol and 0.015% bromophenol blue).

Western blot analysis was performed as described previously (Choy et al. (18); Fan et al. (19)) with some modification. The expression of IGF-II was detected with anti-IGF-II antibody (1–2 μg/ml) (Research Diagnostics Inc., Flanders N.J.) followed by horseradish peroxidase-conjugated anti-goat IgG (sigma, St. Loius Mo.) at a dilution of 1:7,000. Approximately 7.5 kDa protein was visualized by ECL (Amersham, Arlington heights, Ill.)

Figure 4:
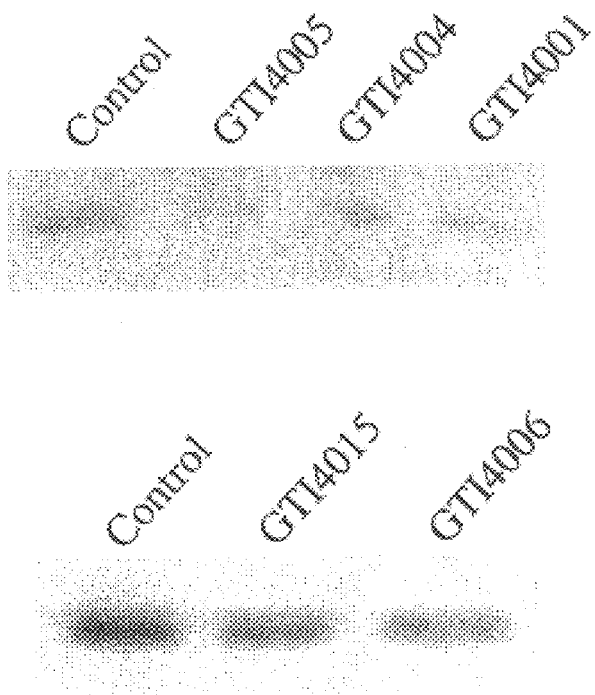
FIG. 4 is a photograph of a Western Blot of IGF-II expression in human neuroblastoma cells after treatment with different antisense oligodeoxynucleotides.

FIG. 4 shows the reduction in IGF-II protein in human neuroblastoma cells after treatment with various antisense oligonucleotides.

Figure 5:
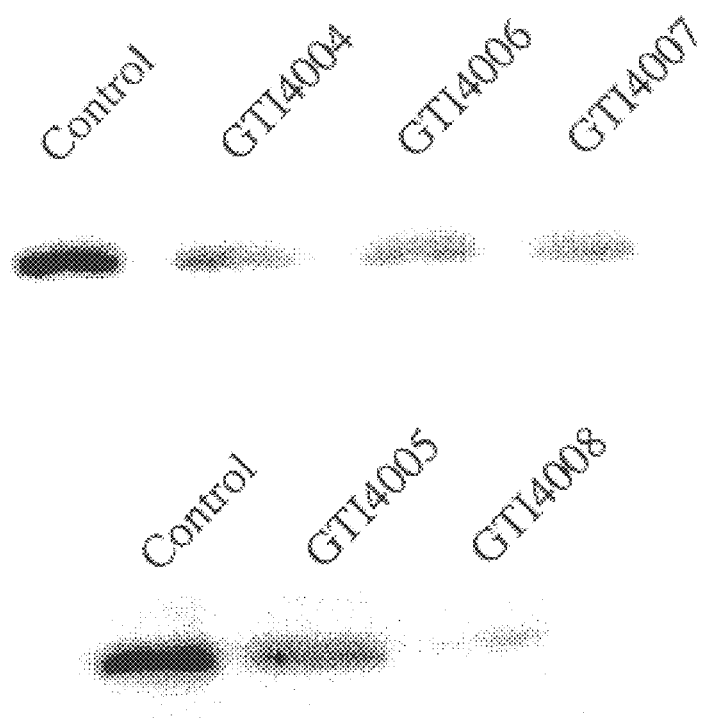
FIG. 5 is a photograph of a Western Blot of IGF-II expression in human rhabdomyosarcoma cells after treatment with different antisense oligodeoxynucleotides.

FIG. 5 shows the reduction in IGF-II protein in human rhabdomyosarcoma cells after treatment with various antisense oligonucleotides.

Example 4

Inhibition of Human Tumor Cell Growth in Mice by Intravenous Treatment with Antisense Oligonucleotides Complementary to IGF-II CD-1 athymic nude mice were purchased from Charles River Laboratories (Montreal Canada). SK-N-AS human neuroblastoma cells (typically $3 \times 10^6$ cells in 100 μl of PBS) were subcutaneously injected into the right flank of 6–7 weeks old CD-1 athymic female nude mice. Each experimental group included 5 mice. After the size of tumor reached an approximate volume of 100 $mm^2$, typically 6 days post tumor cell injection, the various antisense oligonucleotides were administered by bolus infusion into the tail vein every other day at 10 mg/kg. Control animals received saline alone for the same period. Treatments typically lasted 14 days thereafter.

Figure 6A:
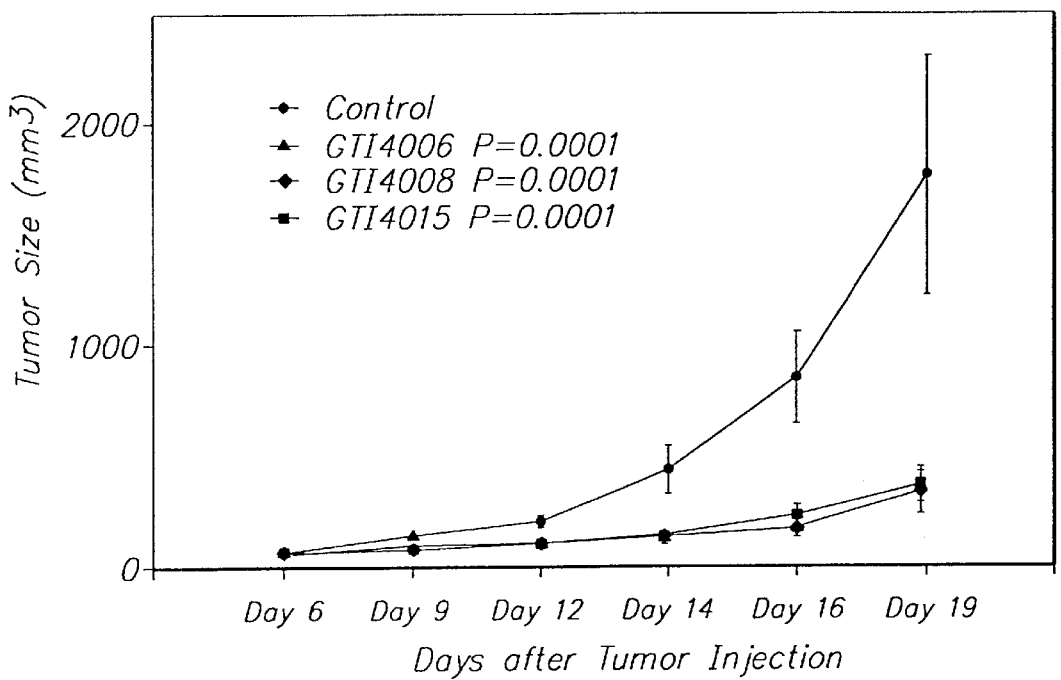
FIG. 6A is a graph of the volume of a tumor following injection of human neuroblastoma cells (SK-N-AS) in mice with administration of various antisense oligonucleotides or without (control).

FIG. 6A shows the effects of the various antisense oligonucleotides on human neuroblastoma tumor growth in CD-1 nude mice. Antitumor activities were estimated by the inhibition of tumor volume, which was measured with a caliper on average of two day intervals over the span of 14 days. Each point in the figure represents mean tumor volume calculated from 5 animals per experimental group. Analysis of covariance was used to compare the regression curves of mice over time within each treatment group. Specific hypothesis of equality of slopes, or equality of intercepts when slopes are equal are derived from the analysis. All analysis used the SAS (Statistical Analysis System) version 6.12. When compared to the saline control, administration of the antisense oligonucleotide inhibited the growth of the tumor with a p value of $\leq 0.0001$.

Figure 6B:
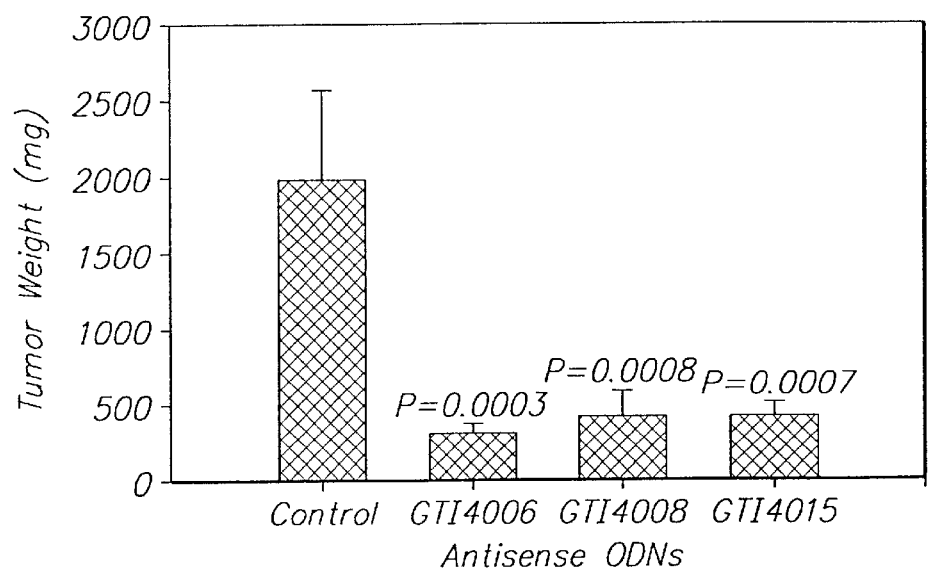
FIG. 6B is a graph of the weight of a tumor 20 days after injection of human neuroblastoma cells (SK-N-AS) in mice with administration of various antisense oligonucleotides or without (control).

At the end of the treatment (usually 24 hours after the last treatment) the animals were sacrificed and tumor weights were measured. FIG. 6B shows the mean weight of the tumors. The antisense oligonucleotides showed significant inhibitory effects on tumor growth. One-way analysis of variance was used to compare the means of groups of treatments. Where the overall group effect was significant, a priori multiple comparisons using the least square means was used to find the pairs of treatment groups that were significantly different. When tumor weight was compared the antisense oligonucleotides also showed statistically significant inhibition when compared to the saline control.

Example 5

Inhibition of Human Tumor Cell Growth in Mice by Intravenous Treatment with Antisense Oligonucleotides Complementary to IGF-II CD-1 athymic nude mice were purchased from Charles River Laboratories (Montreal Canada). G401 human Wilms' tumor cells (typically $3 \times 10^6$ cells in 100 μl of PBS) were subcutaneously injected into the right flank of 6–7 weeks old CD-1 athymic female nude mice. Each experimental group included 5 mice. After the size of tumor reached an approximate volume of 100 $mm^3$, typically 8 days post tumor cell injection, the various antisense oligonucleotides were administered by bolus infusion into the tail vein every other day at 10 mg/kg. Control animals received saline alone for the same period. Treatments typically lasted 18 days thereafter.

Figure 7A:
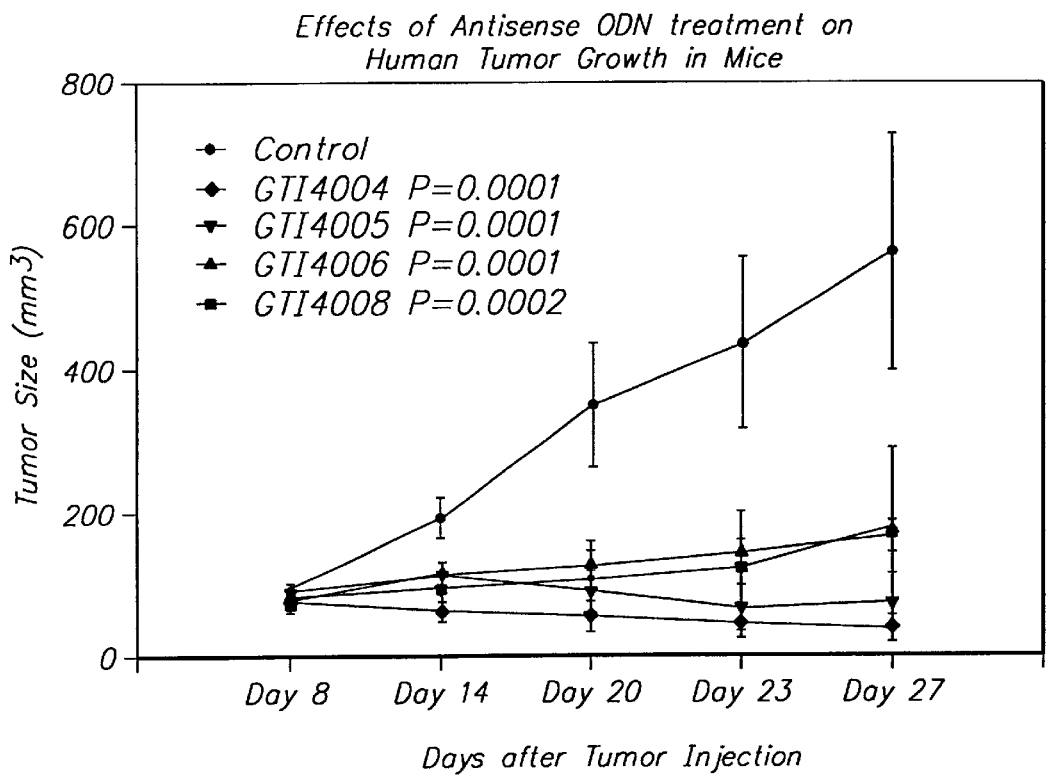
FIG. 7A is a graph of the volume of a tumor following injection of human Wilms' tumor cells (G401) in mice with administration of various antisense oligonucleotides or without (control).

FIG. 7A shows the effects of the various antisense oligonucleotides on human Wilms' tumor growth in CD-1 nude mice. Antitumor activities were estimated by the inhibition of tumor volume, which was measured with a caliper on average of two day intervals over the span of 18 days. Each point in the figure represents mean tumor volume calculated from 5 animals per experimental group. Analysis of covariance was used to compare the regression curves of mice over time within each treatment group. Specific hypothesis of equality of slopes, or equality of intercepts when slopes are equal are derived from the analysis. All analysis used the SAS (Statistical Analysis System) version 6.12. When compared to the saline control, administration of the antisense oligonucleotide inhibited the growth of the tumor with a p value of $\leq 0.0002$.

Figure 7B:
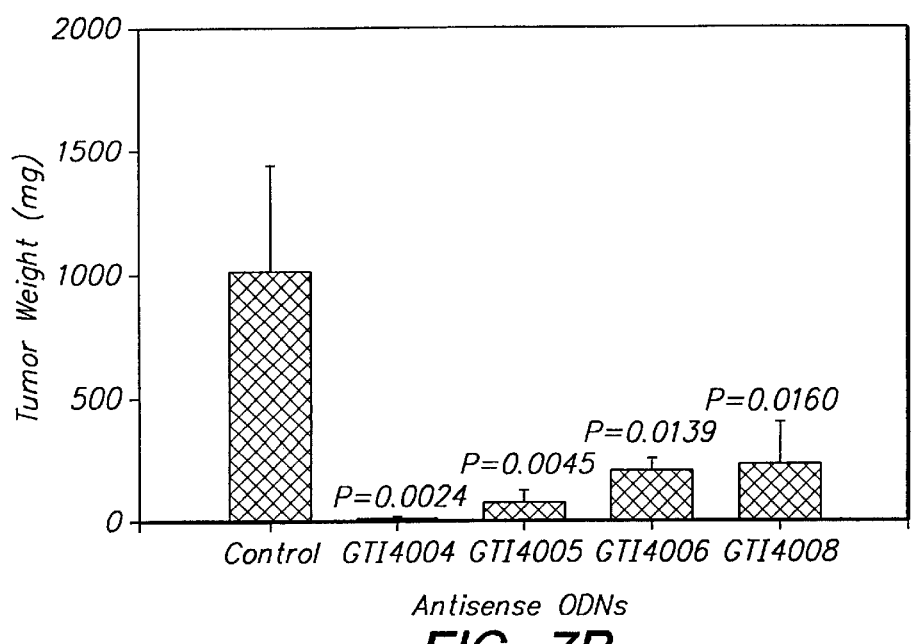
FIG. 7B is a graph of the weight of a tumor 20 days after injection of human Wilms' tumor cells (G401) in mice with administration of various antisense oligonucleotides or without (control).

At the end of the treatment (usually 24 hours after the last treatment) the animals were sacrificed and tumor weights were measured. FIG. 7B shows the mean weight of the tumors. The antisense oligonucleotides showed significant inhibitory effects on tumor growth. One-way analysis of variance was used to compare the means of groups of treatments. Where the overall group effect was significant, a priori multiple comparisons using the least square means was used to find the pairs of treatment groups that were significantly different. When tumor weight was compared the antisense oligonucleotides also showed statistically significant inhibition when compared to the saline control.

Example 6

Reduction in IGF-II mRNA Levels in Human Tumors in Mice by Intravenous Treatment with Antisense Oligonucleotides Complementary to IGF-II CD-1 athymic nude mice were purchased from Charles River Laboratories (Montreal Canada). SK-N-AS human neuroblastoma cells (typically $3 \times 10^6$ cells in 100 μl of PBS) were subcutaneously injected into the right flank of 6–7 weeks old CD-1 athymic female nude mice. Each experimental group included 5 mice. After the size of tumor reached an approximate volume of 100 $mm^3$, typically 6 days post tumor cell injection, the various antisense oligonucleotides were administered by bolus infusion into the tail vein every other day at 10 mg/kg. Control animals received saline alone for the same period. Mice were sacrificed after 7 injections and excised tumor fragments of similar size were immediately collected into TRIzol reagent (GIBCO BRL) and rapidly homogenized for mRNA preparation.

To measure the effects of antisense oligonucleotides on IGF-II mRNA levels, northern blot analysis was performed as previously described (Hurta and Wright (27)) with some modifications. The blots were hybridized with $^{32}$P-labeled 389 bp PCR fragments synthesized using forward primer (5'-TAC CGC CCC AGT GAG ACC CT-3') [SEQ ID NO:32], reverse primer (5'-TGA CGT TTG GCC TCC CTG AA-3') [SEQ ID NO:33] and the human colorectal adenocarcinoma 5'-stretch plus cDNA library (Clonetech, Palo Alto Calif.) as a template. Human IGF-II mRNA was expressed as a ~6 kb nucleotide transcript (Werner et al.[6]) and its levels were compared to glyceraldehyde-3-phosphate dehydrogenase (GADPH) mRNA as previously described (Hurta and Wright (27)).

Figure 8:
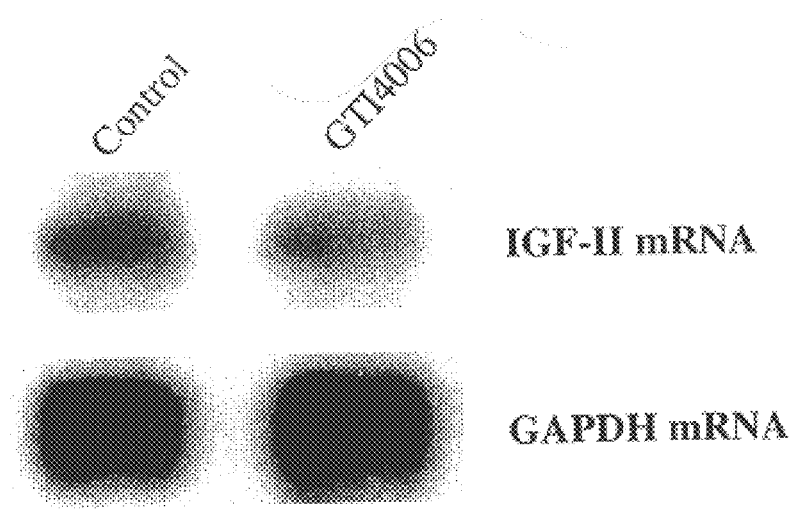
FIG. 8 is an autoradiograph of a Northern Blot of IGF-II mRNA levels in human neuroblastoma (SK-N-AS) tumors following treatment with antisense oligonucleotide GTI4006 [SEQ ID NO:6].

FIG. 8 shows that the level of IGF-II mRNA was reduced in tumor treated with the antisense oligodeoxynucleotide GTI4006 [SEQ ID NO:6].

Example 7

Reduction in IGF-II Protein Levels in Human Tumors in Mice by Intravenous Treatment with Antisense Oligonucleotides Complementary to IGF-II CD-1 athymic nude mice were purchased from Charles River Laboratories (Montreal Canada). SK-N-AS human neuroblastoma cells (typically 3×10$^6$ cells in 100 µl of PBS) were subcutaneously injected into the right flank of 6–7 weeks old CD-1 athymic female nude mice. Each experimental group included 5 mice. After the size of tumor reached an approximate volume of 100 mm$^3$, typically 6 days post tumor cell injection, the various antisense oligonucleotides were administered by bolus infusion into the tail vein every other day at 10 mg/kg. Control animals received saline alone for the same period. Mice were sacrificed after 7 injections and excised tumor fragments of similar size were immediately collected into RIPA extraction buffer (50 mM Tris-HCl, pH 7.5, 150 mM leupeptin) and rapidly homogenized for protein preparation.

To measure the effects of antisense oligodeoxynucleotides on IGF-II protein levels, western blot analysis was performed as previously described (Choy et al. (18), Fan et al. (19)) with some modification. The protein extracts (10–20 µg) were fractionated on a 15% SDS-PAGE gel and transferred to nitrocellulose membranes and visualized by India ink staining. The expression of IGF-II was detected with anti-IGF-II antibody (1–2 µg/ml) (Research Diagnostics Inc., Flanders N.J.) followed by horseradish peroxidase-conjugated anti-goat IgG (sigma, St. Loius Mo.) at a dilution of 1:7,000. Approximately 7.5 kDa protein was visualized by ECL (Amersham, Arlington Heights, Ill.).

Figure 9:
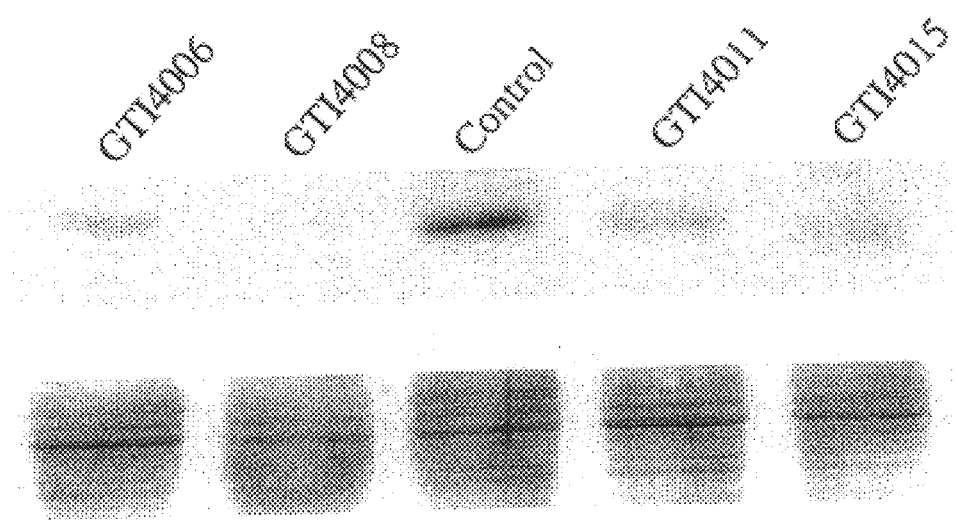
FIG. 9 is a photograph of a Western blot of IGF-II protein levels in human neuroblastoma (SK-N-AS) tumors following treatment with various antisense oligonucleotides. The band below is a photograph of the gel stained with India ink to show the total protein loaded.

FIG. 9 shows the western blot of the protein extracted from the tumor cells. Each of the antisense oligonucleotides tested reduced the IGF-II protein levels in the tumors. A part of the blot stained with India ink is shown underneath to demonstrate an equal loading in each lane.

Example 8

Inhibition of Experimental Metastasis by Antisense Oligonucleotides

Experimental metastasis of C8161 human melanoma cells treated with different antisense oligonucleotides was estimated as previously described (Fan et al., 1996[19]). Aliquots of cell suspension were seeded into 100 mm tissue culture dishes at a density of 2×10$^6$ and incubated overnight at 37° C. in α-MEM medium supplemented with 10% FBS. Cells were washed once in 10 ml of PBS and treated with 0.2 µM of oligonucleotides in the presence of cationic lipid (Lipofectin reagent, final concentration, 5 µg/ml, Gibco-BRL) for 4 hours. The antisense oligonucleotides were removed by washing the cells once with PBS and the cells were trypsinized. Cells were then collected by centrifugation, and approximately 1×10$^5$ cells suspended in 0.1 ml of PBS were injected into the tail veins of 6–8 week old CD-1 athymic female nude mice. Estimates of the number of lung tumors were made 5 weeks later, after excised lungs from individual mice were stained with picric acid dye solution (75% picric acid, 20% formaldehyde, 5% glacial acetic acid).

Figure 10:
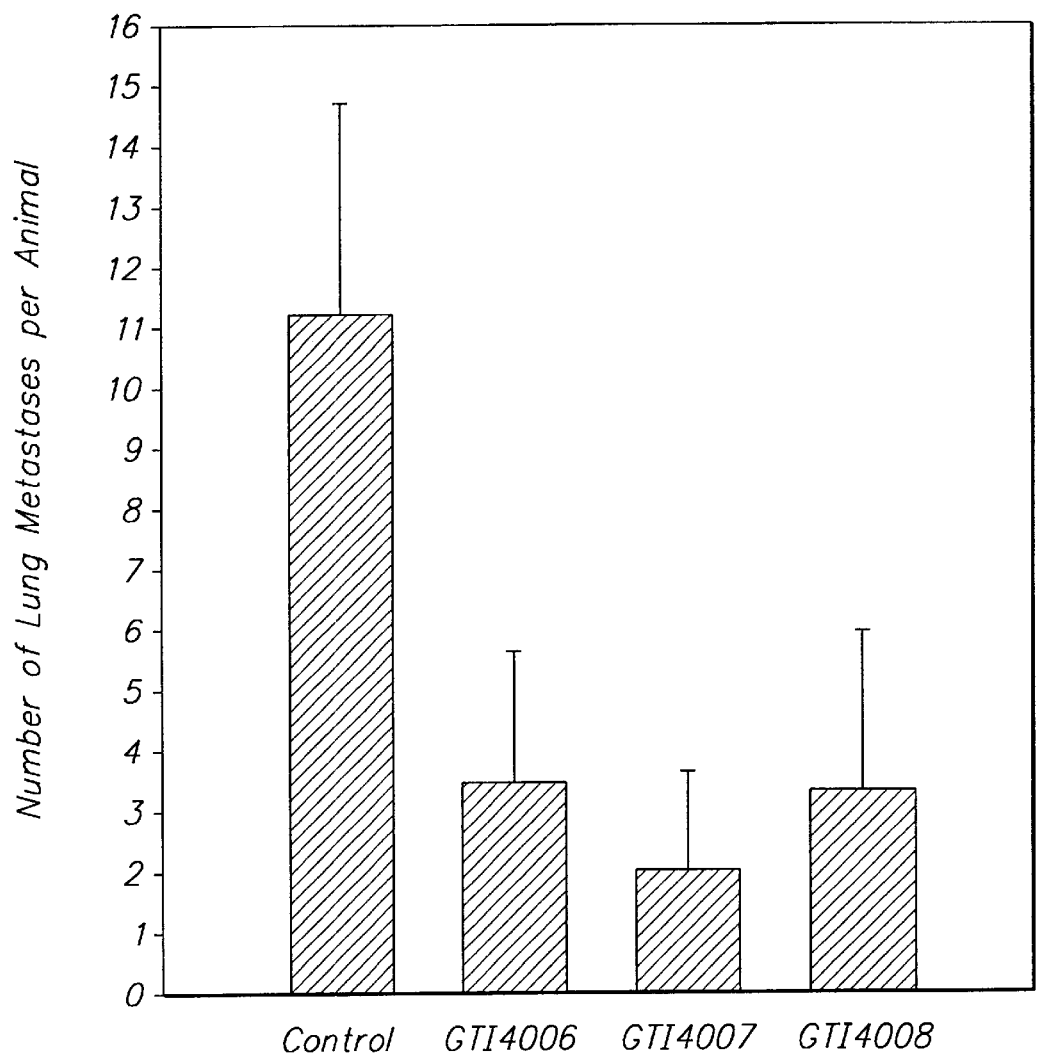
FIG. 10 is a graph of the average number of lung metastases per mouse by the human melanoma cell line (C8161) after treatment of the cell line with the various antisense oligonucleotides.

FIG. 10 shows the reduced number of lung tumors in the female nude mice after treatment of the tumor cells with the various antisense oligodeoxynucleotides.

What is claimed is:

1. An antisense oligonucleotide comprising from about 7 to about 100 nucleotides wherein the oligonucleotide comprises a sequence complementary to the 5' untranslated region consisting of exons 4, 5 or 6 of human fetal IGF-II mRNA with the proviso that the sequence does not consist of SEQ ID NO:2 and wherein the antisense oligonucleotide inhibits IGF-II expression.

2. The antisense oligonucleotide of claim 1 further comprising one or more phosphorothioate internucleotide linkages.

3. The antisense oligonucleotide of claim 1 further comprising additional nucleotides not complementary to the IGF-II mRNA.

4. The antisense oligonucleotide of claim 1 wherein the sequence is selected from the group consisting of SEQ ID Nos: 1 and 3–15.

5. The antisense oligonucleotide of claim 1 wherein the antisense oligonucleotide comprises from about 7 nucleotides to about 50 nucleotides.

6. A vector comprising an antisense oligonucleotide sequence from about 7 to 100 nucleotides comprising a sequence complementary to the 5' untranslated region consisting of exons 4, 5 and 6 of human fetal IGF-II mRNA, wherein the antisense oligonucleotide inhibits IGF-II expression.

7. The vector according to claim 6 wherein the antisense oligonucleotide comprises from about 7 to about 50 nucleotides.

8. A pharmaceutical composition comprising a pharmaceutically acceptable excipient and an effective amount of an antisense oligonucleotide from about 20 to 100 nucleotides comprising a sequence complementary to the 5' untranslated region consisting of exons 4, 5 and 6 of human fetal IGF-II mRNA, wherein the antisense oligonucleotide inhibits IGF-II expression.

9. The pharmaceutical composition according to claim 8 wherein the sequence is selected from the group consisting of SEQ ID NOs: 1–15.

10. The pharmaceutical composition according to claim 8 wherein the antisense oligonucleotide comprises from about 20 to about 50 nucleotides.

11. A method for inhibiting the growth of a human tumor comprising administering to a human suspected of having the tumor an effective amount of an antisense oligonucleotide comprising from about 20 to about 100 nucleotides comprising a sequence complementary to the 5' untranslated region consisting of exons 4, 5, and 6 of human fetal IGF-II mRNA under conditions such that the growth of the tumor is inhibited.

12. The method according to claim 11 further comprising the step of administering to the human a chemotherapeutic agent.

13. The method according to claim 11 wherein the oligonucleotide comprises a sequence selected from the group consisting of SEQ ID NOs: 1–15.

14. The method according to claim 11 wherein the oligonucleotide is nuclease resistant.

15. The method according to claim 11, wherein the antisense oligonucleotide comprises from about 20 to about 50 nucleotides.

16. An antisense oligonucleotide comprising from about 20 to about 100 nucleotides wherein the oligonucleotide comprises a sequence selected from the group consisting of SEQ ID NOs: 17–31.

17. The antisense oligonucleotide of claim 16 further comprising one or more phosphorothioate internucleotide linkages.

18. The antisense oligonucleotide of claim 16 further comprising additional nucleotides not complementary to the IGF-II mRNA.

19. A vector comprising an antisense oligonucleotide sequence from about 20 to 100 nucleotides comprising a sequence selected from the group consisting of SEQ ID NOs: 17–31 in Table 2.

20. A composition comprising a pharmaceutically acceptable excipient and an effective amount of an antisense oligonucleotide from about 20 to 100 nucleotides comprising a sequence selected from the group consisting of SEQ ID NOs: 17–31.

* * * * *